United States Patent
Morgan et al.

(10) Patent No.: US 10,136,967 B2
(45) Date of Patent: Nov. 27, 2018

(54) DENTAL IMPLANT ABUTMENT COPINGS

(71) Applicant: Bicon, LLC, Boston, MA (US)

(72) Inventors: Vincent J. Morgan, Boston, MA (US);
Robert E. Vasile, Westborough, MA (US)

(73) Assignee: Bicon, LLC, Boston, MA (US)

( * ) Notice: Subject to any disclaimer, the term of this patent is extended or adjusted under 35 U.S.C. 154(b) by 102 days.

(21) Appl. No.: 15/065,460

(22) Filed: Mar. 9, 2016

(65) Prior Publication Data
US 2017/0258558 A1   Sep. 14, 2017

(51) Int. Cl.
*A61C 8/00* (2006.01)
*A61C 13/00* (2006.01)

(52) U.S. Cl.
CPC .......... *A61C 8/0059* (2013.01); *A61C 8/0056* (2013.01); *A61C 8/0066* (2013.01); *A61C 8/0072* (2013.01); *A61C 8/0074* (2013.01); *A61C 13/0019* (2013.01)

(58) Field of Classification Search
CPC ... A61C 8/0048; A61C 8/0056; A61C 8/0066; A61C 8/0072; A61C 8/0074; A61C 13/0019; A61C 8/0071; A61C 8/0095; A61C 8/004
See application file for complete search history.

(56) References Cited

U.S. PATENT DOCUMENTS

| | | | | |
|---|---|---|---|---|
| 5,135,395 A | * | 8/1992 | Marlin | A61C 8/0048 433/173 |
| 5,527,182 A | * | 6/1996 | Willoughby | A61C 8/0001 433/172 |
| 6,299,447 B1 | * | 10/2001 | Zuest | A61C 8/0048 433/172 |
| 6,325,628 B1 | * | 12/2001 | Morgan | A61C 8/0048 433/173 |

(Continued)

FOREIGN PATENT DOCUMENTS

WO   WO2009/075459   6/2009
WO   WO2017/156281   9/2017

OTHER PUBLICATIONS

International Search Report and Written Opinion dated Jul. 10, 2017, in corresponding PCT Application No. PCT/US17/21589, pp. 1-16.

*Primary Examiner* — Nicholas Lucchesi
(74) *Attorney, Agent, or Firm* — Fish & Richardson P.C.

(57) ABSTRACT

A dental abutment coping or ring for securing a dental prosthesis to dental abutments. The coping or ring includes a body for insertion into a dental prosthesis, and a cavity or space sized to accept a head of the dental abutment. The interior surface of the cavity includes an interface region sized and shaped to accept the dental abutment in a retentive interface fit or a passive fit, depending on an angle of the interface surface. The exterior surface can have channels configured to contain a cement bonding the exterior surface (Continued)

to the dental prosthesis. A dental prosthesis system including the dental copings provides a retentive interference fit between the prosthesis and the dental abutments, even where the dental abutments are not parallel. A plurality of copings and abutments enables a retentive fit to varying degrees depending on the degree of interference fit in each coping and abutment.

25 Claims, 19 Drawing Sheets

(56) References Cited

U.S. PATENT DOCUMENTS

| | | | |
|---|---|---|---|
| 8,714,977 B2* | 5/2014 | Fromovich | A61C 8/0022 433/174 |
| 2002/0028425 A1* | 3/2002 | Hurson | A61C 8/0001 433/202.1 |
| 2002/0031749 A1* | 3/2002 | Morgan | A61C 8/005 433/173 |
| 2003/0082499 A1* | 5/2003 | Halldin | A61C 8/0001 433/173 |
| 2006/0014120 A1* | 1/2006 | Sapian | A61C 8/0057 433/173 |
| 2009/0317769 A1* | 12/2009 | Urdaneta | A61C 8/005 433/202.1 |
| 2011/0262884 A1* | 10/2011 | Zena | A61C 8/0001 433/201.1 |
| 2011/0306014 A1* | 12/2011 | Conte | A61C 8/0001 433/173 |
| 2012/0214130 A1* | 8/2012 | Krivoruk | A61C 8/0048 433/173 |

* cited by examiner

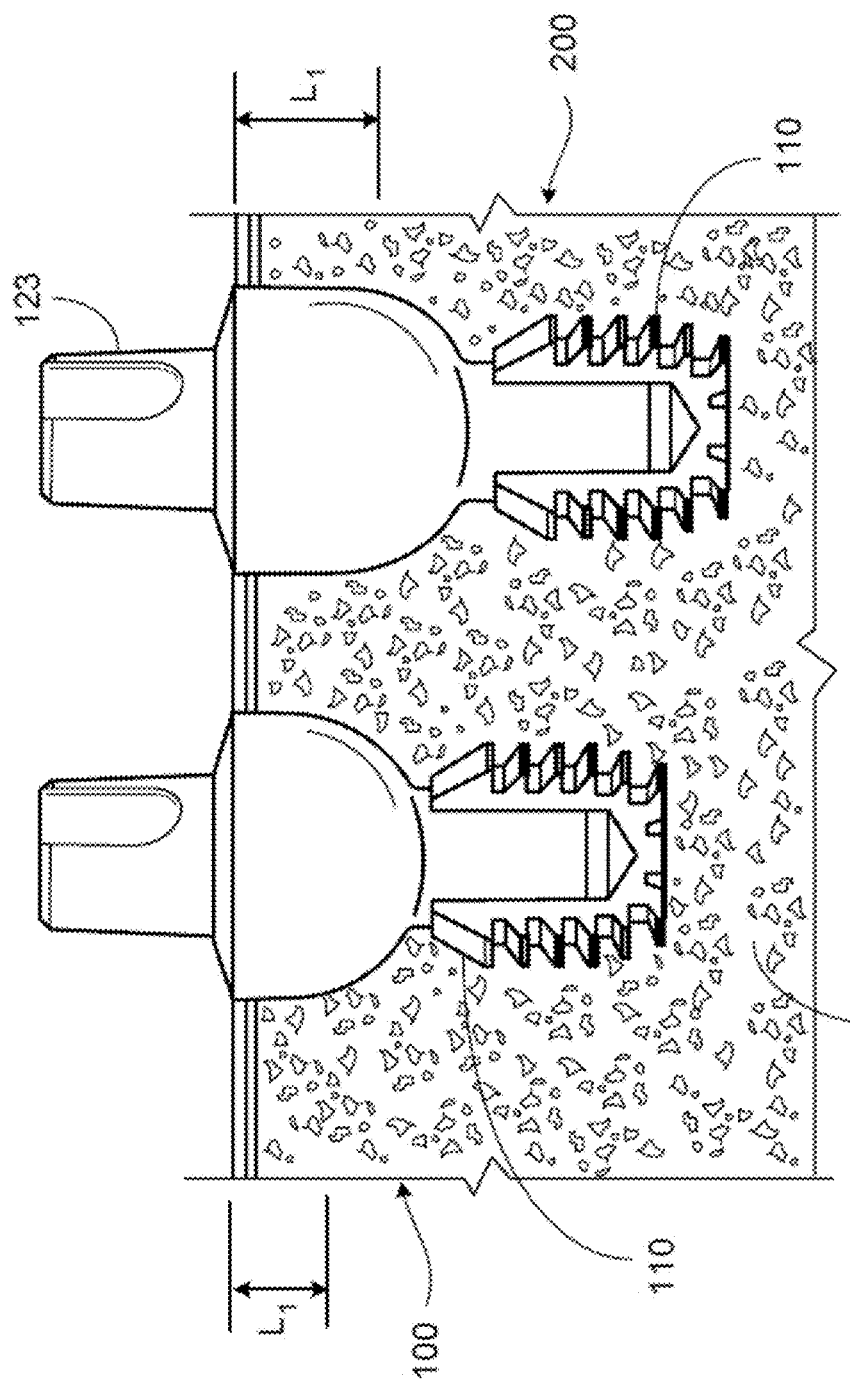

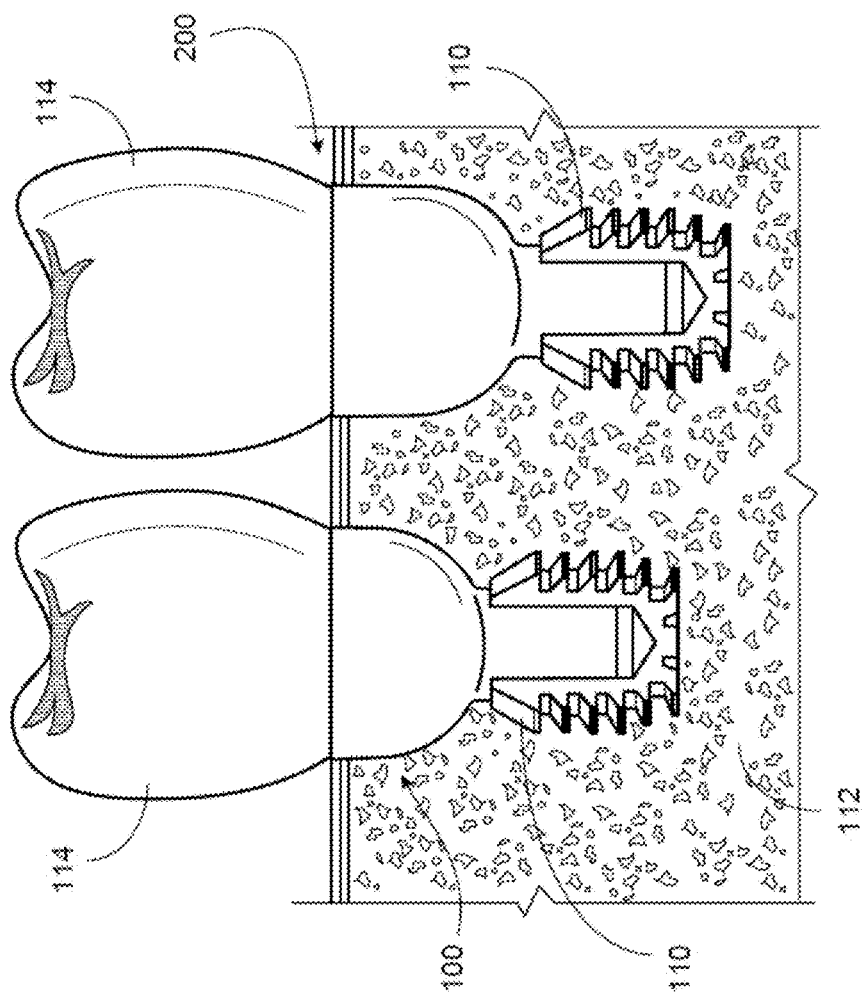

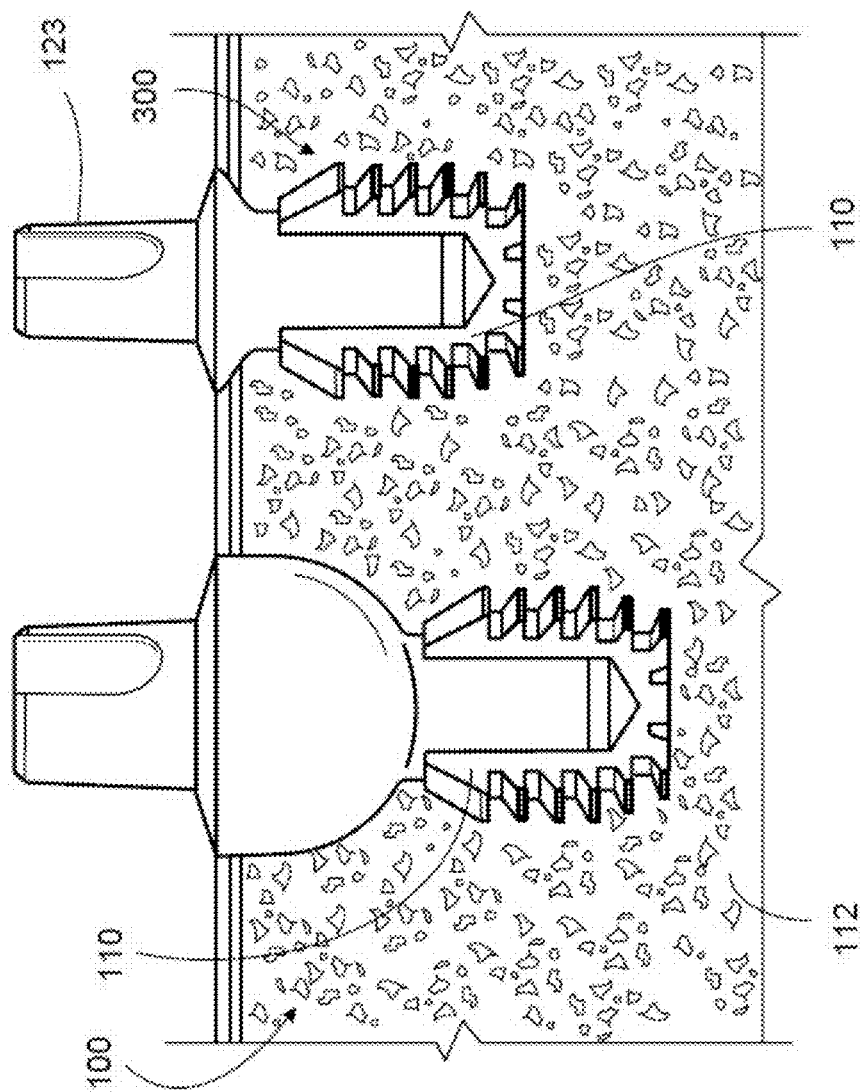

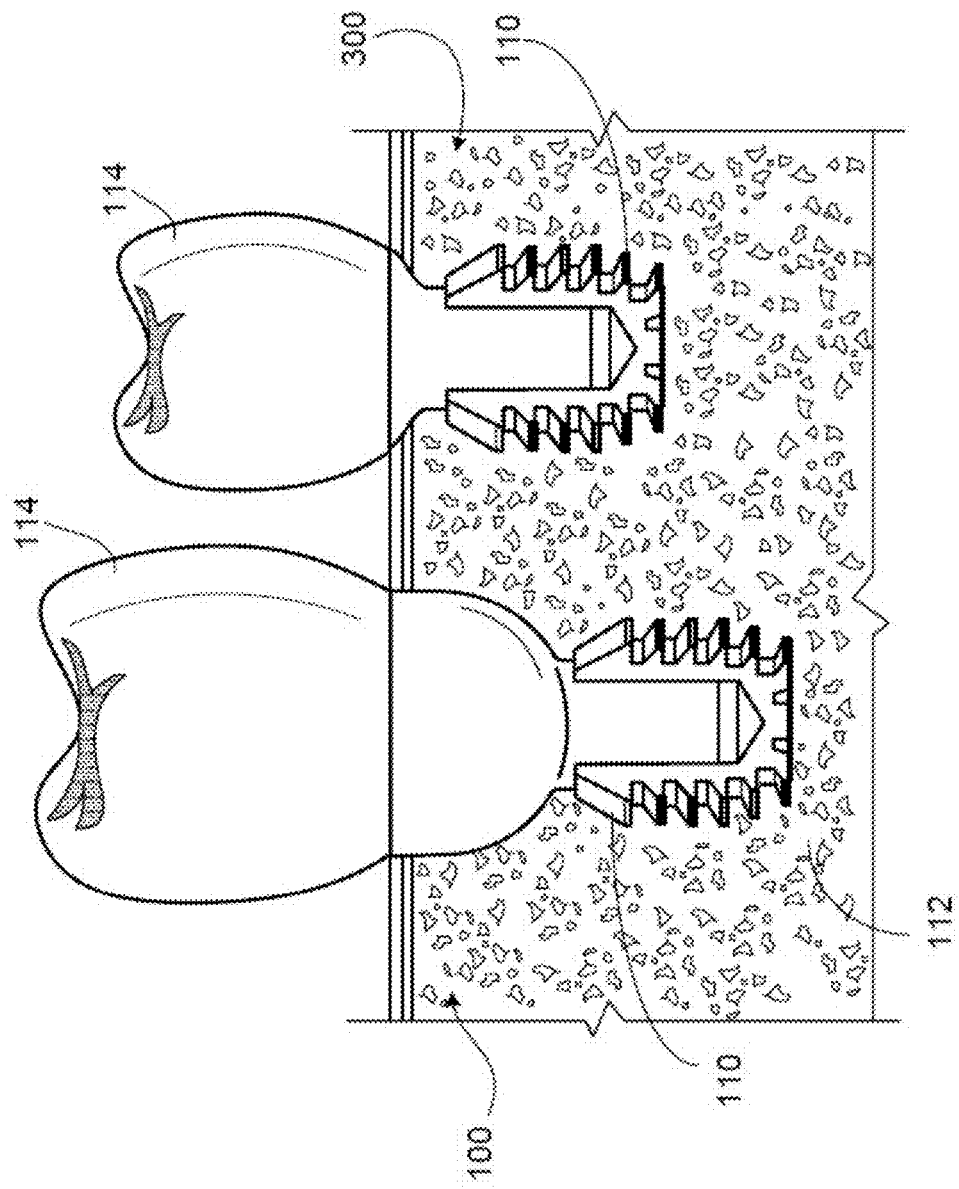

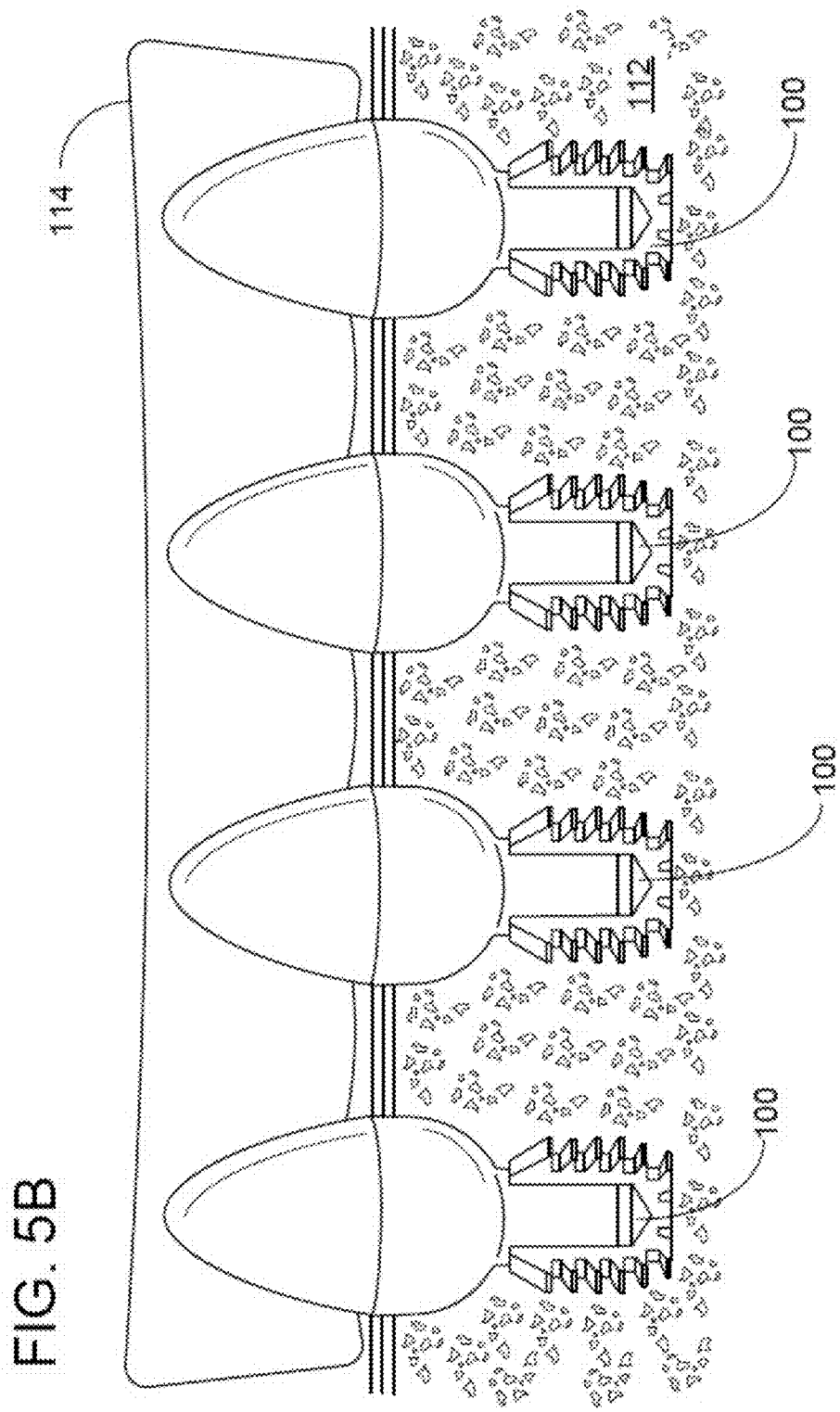

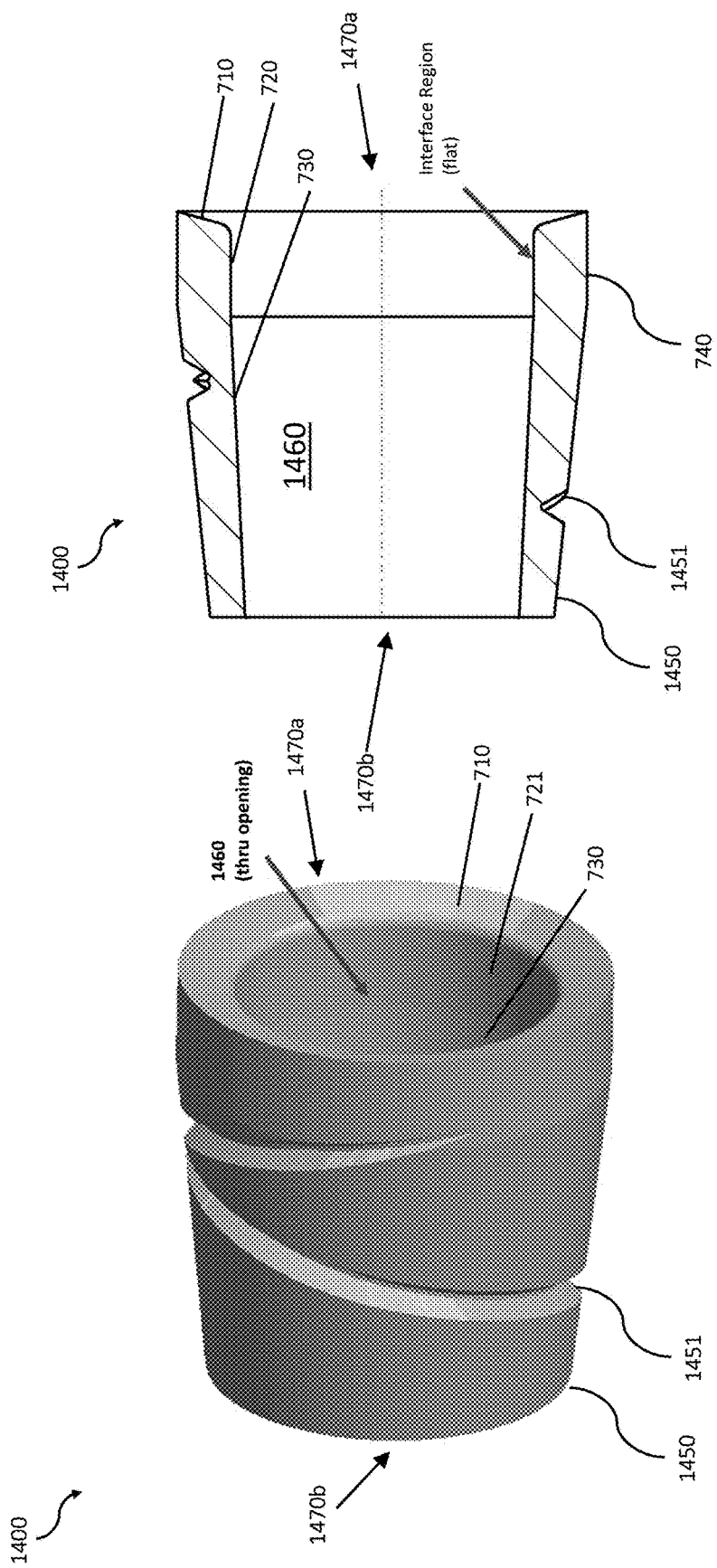

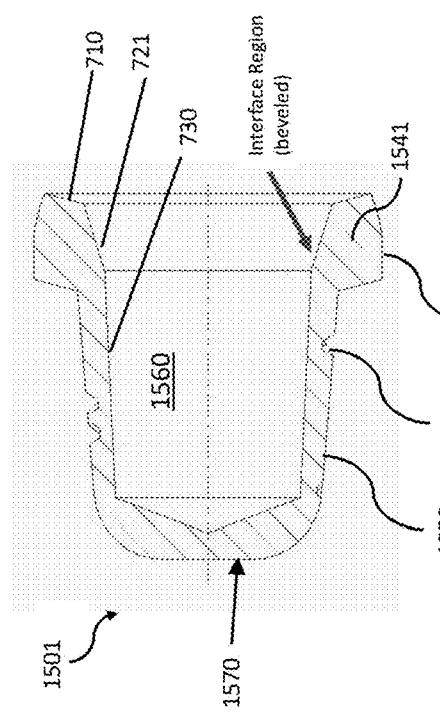
FIG. 15C
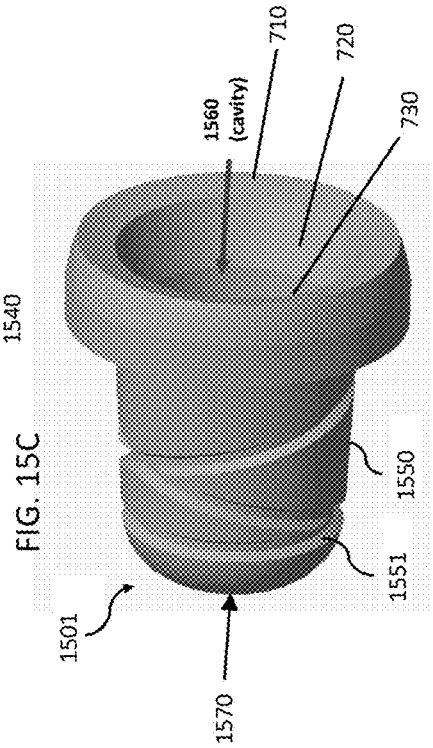
FIG. 15D
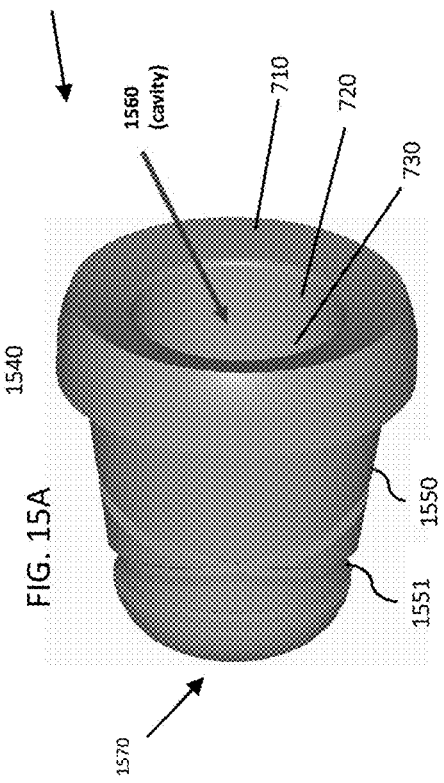
FIG. 15A
FIG. 15B

DENTAL IMPLANT ABUTMENT COPINGS

FIELD

The present disclosure concerns copings for securing a dental prosthesis to a plurality of dental implant abutments.

BACKGROUND

Dental implants are often the best treatment for missing teeth. When a tooth is removed, both the visible part of the tooth, called the crown, and the root are lost.

A dental implant can be placed in the jawbone so that it can be fused with natural bone and become a strong and sturdy foundation for replacement teeth. Implants can be used to replace an individual tooth or for an implant-supported bridge or denture containing multiple teeth.

A dental implant abutment is a device that connects the prosthetic tooth/teeth to the dental implant. The replacement tooth is custom made to match a patient's natural teeth and is sometimes referred to as a crown or dental prosthesis.

SUMMARY OF THE INVENTION

An example embodiment of the present invention is a dental abutment coping for securing a dental prosthesis to a dental abutment. The dental abutment coping has a body extending from a closed or open end to an open end along a longitudinal axis and the body includes a cavity extending from an opening in the open end of the dental abutment coping. The body has an exterior surface adapted to be inserted into a corresponding interface cavity of the dental prosthesis, a peripheral region of the open end extending around the opening and having a beveled surface oriented towards the longitudinal axis at an angle relative to the longitudinal axis, and an interior surface sized to accept a prosthetic head of the dental abutment. The interior surface has a tapered interior region and an interface interior region, with the interface interior region being between the peripheral region and the tapered interior region. The tapered interior region defines an increasing internal diameter of the cavity between a closed end of the cavity and the interface interior region. The angle of the beveled surface may be between 12° and 18° relative to the longitudinal axis. In some embodiments, the dental abutment coping is symmetric about the longitudinal axis with respect to the longitudinal axis.

In some embodiments, the exterior surface includes one or more channels configured to contain a mechanical or an adhesive bond of the exterior surface to the dental prosthesis. The channels may be two counter-rotating spiral channels.

In some embodiments, the exterior surface includes a tapered exterior region extending along the longitudinal axis, and the tapered exterior region forms an increasing exterior diameter of the body along the central axis. In some embodiments, the exterior surface further includes a flat exterior region having a surface parallel the longitudinal axis, with the tapered exterior region extending from the closed end to the flat exterior region, and the tapered exterior region forming an increasing exterior diameter of the body from the closed or open end to the flat exterior region. The taper angle may be between 3° and 8°.

In some embodiments, the interface interior region is positioned adjacent to both the peripheral region and the tapered interior region.

In some embodiments, the interface interior region has an interface surface substantially parallel to the longitudinal axis.

In some embodiments, the interface interior region comprises a second beveled surface oriented inward (towards the longitudinal axis) at an angle relative to the longitudinal axis. The angle of the second beveled surface may be greater than the angle of first beveled surface.

Another example embodiment is a dental prosthesis system having a plurality of dental abutments, a dental prosthesis including a plurality of interface cavities, a first dental abutment coping, and a second dental abutment coping. The first and second coping have a body extending from a closed or open end to an open end along a longitudinal axis, the body defines a cavity extending from an opening in the open end of the first and second dental abutment copings. The bodies of the first and second copings having an exterior surface adapted to be inserted into one of the interface cavities of the dental prosthesis, a peripheral region of the open end extending around the opening and having a first beveled surface oriented towards the longitudinal axis, and an interior surface sized to accept a head of each of the plurality of dental abutments, the interior surface having a tapered interior region and an interface interior region, the interface interior region being between the peripheral region and the tapered interior region, and the tapered interior region defining an increasing internal diameter of the cavity between a closed or open end of the cavity and the interface interior region. The interface region of the first coping having an interface surface substantially parallel to the first longitudinal axis and the interface region of the second coping includes a second beveled surface oriented towards the longitudinal axis at an angle relative longitudinal axis.

In some embodiments, the exterior surfaces of the first and second dental abutment copings includes one or more channels containing a mechanical or an adhesive bond of the exterior surface to the dental prosthesis.

In some embodiments, the plurality of dental abutments includes a retention element with a base oriented towards an apical end of the dental implant and a shoulder oriented towards a coronal end of the dental abutment at an angle relative a second longitudinal axis such that the perimeter of the retention element increases with increasing distance from the coronal end of the dental abutment through the region of the shoulder, a post extending from the apical end of the dental abutment to the base of the retention element, and a head extending from the coronal end of the dental abutment to the shoulder of the retention element.

In some embodiments, the heads of the plurality of dental abutments have a cone angle between 3° and 8°, and the tapered exterior region of the first and second copings have a taper angle between 2° and 4°.

In some embodiments, the shoulders of the dental abutments are oriented at an angle of at least 12.5° relative to the central axis of each dental abutment, and the angle of the first beveled surface of the first and second copings is at least 12.5° relative to their longitudinal axis.

In some embodiments, each dental abutment further includes a cylindrical neck element between the head and the retention element, the interface surface of the first coping accepts the neck element of a first dental abutment in a retentive friction fit, and the second beveled surface of the second coping accepts the neck element of a second dental abutment.

Another example embodiment is a method of attaching a removable dental prosthesis to a plurality of dental abutments using a corresponding plurality of copings. The method includes placing one of the copings on each of the plurality of dental abutments, applying a mechanical locking or an adhesive to the exterior surface of each coping, pressing the copings into corresponding interface cavities in the dental prosthesis, bonding the copings to the dental prosthesis, and removing the dental prosthesis and bonded coping from the plurality of dental abutments. In some embodiments, the plurality of dental abutments are non-parallel, and at least one of the plurality of dental abutments is in a retentive interface fit with one of the corresponding plurality of copings, and at least one of the plurality of dental abutments is in passive fit with one of the corresponding plurality of copings.

BRIEF DESCRIPTION OF DRAWINGS

FIGS. 3A and 3B show two dental abutments of different sizes with and without a crown.

FIGS. 4A and 4B show two dental abutments of different configurations with and without a crown.

FIGS. 5A-5C show a dental prosthesis supported by multiple dental abutments.

FIGS. 14A and 14B are, respectively, perspective and side cross-section views of a retentive-fit dental abutment coping having a thru opening.

FIGS. 15A-D are perspective and cross-sections views of a passive and retentive copings having an exterior shoulder.

DETAILED DESCRIPTION

Figure 1A:
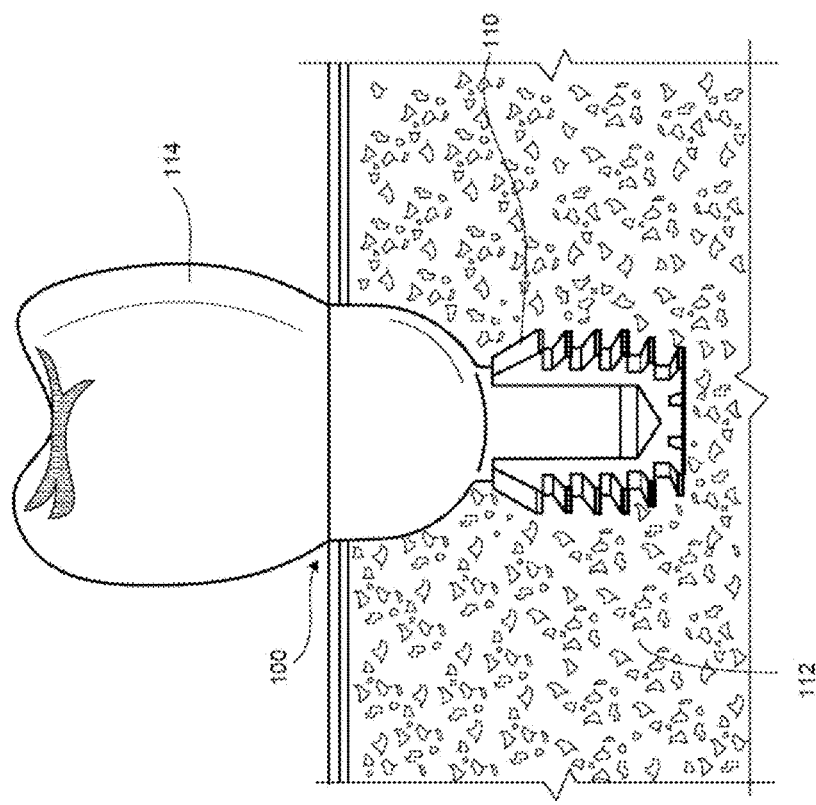
FIGS. 1A and 1B show a dental implant and dental abutment before and after the addition of a crown, respectively.
Figure 1B:
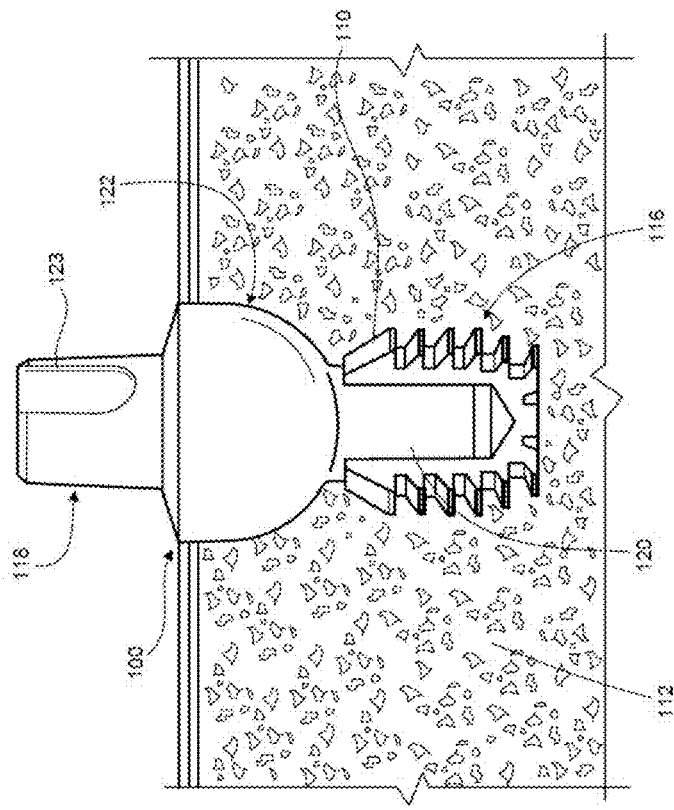

FIG. 1A shows a dental abutment 100 engaged in a dental implant 110 which has been placed in a patient's jawbone 112. FIG. 1B shows the dental abutment 100 and the dental implant 110 after a crown 114 has been placed on the dental abutment 100.

The dental abutment 100 in FIG. 1A extends from the apical end 116 (i.e. toward the jaw) to the coronal end 118 (i.e. toward the crown) in the longitudinal direction. The dental abutment 100 has a post 120, which is designed to be received by the open end of the dental implant 110. The post 120 extends from the apical end 116 of the dental abutment 100 to a retention element 122. The dental abutment 100 also has a coronal portion (or head) 123 which designed to support the crown 114. The coronal portion 123 extends from the coronal end 118 of the dental abutment 100 to the retention element 122.

The dental abutment 100 can be made out of a variety of materials, including titanium alloy or polyether ether ketone (PEEK).

Figure 2C:
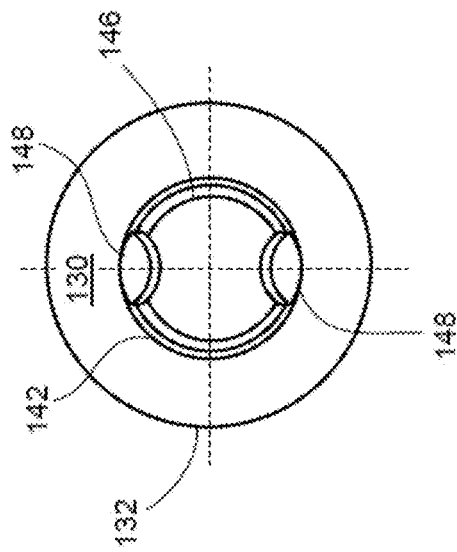
FIGS. 2B and 2C depict the cross section and coronal views of the abutment in FIG. 2A, respectively.
Figure 2B:
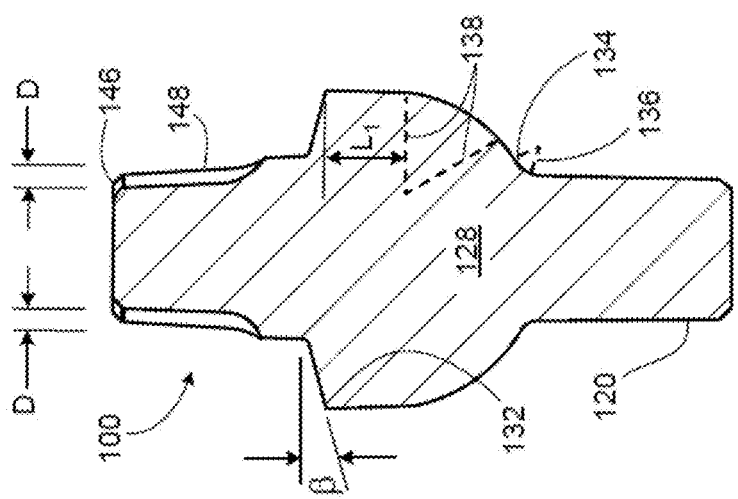
Figure 2A:
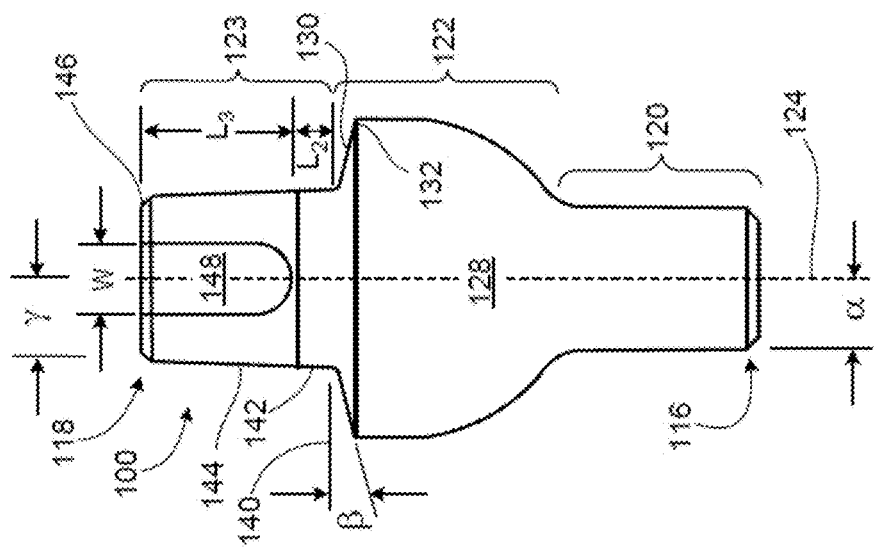
FIG. 2A is a side view of a dental abutment.

FIGS. 2A-2C shows the dental abutment 100 in isolation to more clearly illustrate features of the dental abutment 100.

The post 120 is substantially cylindrical, which allows for the 360° rotation of the dental abutment 100 while it is being seated into the dental implant 110 (see FIGS. 1A and 1B) in order to facilitate a dentist's correct orientation of the prosthesis or crown 114 (see FIG. 1B), either intra-orally or extra-orally. This cylindrical shape provides the opportunity for the prosthesis to be used to orient and initially seat the abutment in the well of the implant. The simplicity of the cylindrical shape affords for improved manufacturability and also makes the dental abutment 100 compatible with a number of different types of dental prostheses. While substantially cylindrical, the post 120 is tapered to provide a friction fit connection which is a locking taper between the post 120 and the dental implant 110 (see FIGS. 1A and 1B). This configuration can facilitate seizing, galling or cold welding between the post 120 and the dental implant 110.

Once fully engaged, this mechanism limits or prevents unintentional rotation and micro-movement between the dental abutment 100 and dental implant 110 (see FIGS. 1A and 1B). The locking taper can also provide a bacterial seal between the two components. The angle α between sides of the post 120 and a longitudinal axis 124 of the dental abutment 100 is approximately 1.3°. Depending on the dental abutment variant, the angle between sides of the post 120 and a longitudinal axis 124 of the dental abutment 100 is typically between 1.1° and 1.6°. The geometry of the dental abutment 100 is symmetrical along the longitudinal axis 124.

The retention element 122 extends from the post 120 to the coronal portion 123. The retention element 122 has a base 128 and a shoulder 130 which meets the base 128 at a margin 132. The transition between the base 128 and the post 120 is a curve 134 with a radius of curvature 136 (see FIG. 2B) of approximately 0.02 inches. In some dental abutments, the radius of curvature 136 is more or less than 0.02 inches (e.g., between 0.01 and 0.03 inches) which can reduce stress factors and resulting fractures. The surface of the base 128 has a radius of curvature 138 (see FIG. 2B) of approximately 0.08 inches. In some dental abutments, the radius of curvature 138 is more or less than 0.08 inches (e.g., between 0.08 and 0.15 inches). The shape of the base 128 provides for the consistent confrontation of what is an approximation of a hemispherical contour to tissues in the proximity to the periosteum. This confrontation in turn can stimulate osteoblastic activity and subsequent bone growth.

Between the hemisphere and the shoulder 130, the side of the abutment extends for a length $L_1$ to the margin 132. The perimeter (e.g., circumference) of the dental abutment increases at 1-2° in this portion of the dental abutment as distance from the apical end 116 of the dental abutment 100. In the dental abutment 100, the length $L_1$ is 0.16 inches (4 mm). As discussed in more detail below with reference to FIGS. 3A and 3B, some dental abutments are configured in which the length $L_1$ is more or less than 0.16 inches (4 mm) (e.g., between 0.05 (1.3 mm) and 0.32 inches (8.1 mm)). This variability provides the opportunity to use the same inferior or post and superior or head contours on the abutment, while providing the flexibility to use with implants placed at different depths within the jaw bone.

The diameter of the dental abutment at the margin 132 is 0.24 inches (6 mm). In some dental abutments, the diameter of the dental abutment at the margin 132 is more or less than 0.24 inches (6 mm) (e.g., between 0.16 inches (4 mm) and 0.31 inches (8 mm).

An angle β is defined between the shoulder 130 and a plane 140 that is perpendicular to the longitudinal axis 124. In dental abutment 100, the angle β is approximately 15°. In some dental abutments, the angle β is more or less than 15° (e.g., between 10° and 20°). It has been found that dental abutments in which the angle β is approximately 15° allow the scanning to be performed without any additional modifications or interpretations to the scan.

The coronal portion 123 includes a neck 142, an anti-rotation portion 144, and a bevel 146 at the coronal end of the dental abutment 100. The neck 142 has a length $L_2$. The neck 142 is substantially cylindrical with sides that are substantially parallel to the longitudinal axis 124 of the dental abutment 100. Some dental abutments have necks with other shapes such as, for example, with rectangular or octagonal (rather than circular) cross-sections.

In contrast, the anti-rotation portion 144 of the coronal portion 123 is tapered with a cone angle γ such that the perimeter (e.g., circumference) of the coronal portion 123 at the coronal end of the anti-rotation portion 144 is smaller than the apical end of the anti-rotation portion 144. In dental abutment 100, the cone angle γ is approximately 3°. In some dental abutments, the angle γ is more or less than 3° (e.g., between 3° and 8°). It has been found that dental abutments in which the angle γ is more than 3° help enable scanning to be performed without any additional modifications or interpretations to the scan.

The surface of coronal portion 123 can be either rough or smooth based on the individual needs dictated by the procedure. A roughened surface can be achieved, for example, through the use of grit blasting. This provides a better surface for the adhesion of dental materials, such as opaque (i.e., composite dental resin that is used to cover unsightly dentition), as well as the crown 114 or prosthesis to the coronal portion 123. In particular, the roughened surface can facilitate the mechanical retention of chemical bonding agents such as opaque layers of composite resins or prosthetic cementing agents.

The structure of the coronal portion 123 provides the dental abutment 100 with a configuration that can be easily scanned. The perimeter (e.g., the circumference) of the dental abutment 100 increases monotonically from the coronal end 118 to the margin 132 defined between the base 128 and the shoulder. The edge between the bevel 146 and the anti-rotation portion 144 is smaller than the edge between anti-rotation portion 144 and the neck 142. The edge between the anti-rotation portion 144 and the neck 142 is smaller than margin 132 between the neck 142 and the base 128. As can be seen best in FIG. 2C, the shoulder 130 is visible and clearly delineated which makes the shoulder 130 easy to record during digital scanning. In addition, the length $L_3$ (from the bevel 146 to the neck 142 of the coronal portion 123) is long enough that when present in concert with angle γ, allows all the edges of the dental abutment to be observed with a digital scanner without additional modifications or interpretations to the scan. Unlike abutments whose geometry preclude the use of digital scanning or require modification or interpretations of scanned images for use, the abutments presented in this application allow for easy digital scanning which enables the rapid and precise restorations of a tooth or teeth. This feature supports movement of the dental implant field toward customizable restorations or prostheses and digital dentistry with the increased use of CAD/CAM technologies.

The geometry of these dental abutments not only facilitate their recording by digital scanning technologies, but also allows for a singular conventional recording sleeve configuration to suffice for registering multiple different abutment dimensions. Further conventional dental impression materials can be used to record and represent their multiple different abutment dimensions prosthetically.

The anti-rotation portion 144 of the coronal portion 123 includes anti-rotation features in the form of two grooves 148 on opposite sides of the coronal end 118. The anti-rotational features help control the orientation of a prosthetic component or crown 114 which helps provide a precise fit of the prosthesis. The grooves also guide the prosthetic component or crown 114 into the correct orientation.

The anti-rotation grooves 148 located on opposite sides of the coronal end 118 of the dental abutment 100 are generally of a constant depth that slopes toward the shoulder to end the anti-rotational element. The sloping of the groove is symmetric to reduce material stress.

The length $L_3$ (see FIG. 2A) of the anti-rotation portion 144 and the grooves 148 are nominally 0.125 inches (3.2 mm). The width W (see FIG. 2A) of the grooves 148 is nominally 0.055 inches (1.4 mm). The depth D (see FIG. 2B) of the grooves 148 is nominally 0.02 inches (0.51 mm). As discussed above, the anti-rotation portion 144 of the coronal portion 123 is tapered with an angle γ of approximately 3°. The angled surface allows the anti-rotational element (e.g., grooves 148) to work properly. In addition, the sloping surface facilitates attaching other components as it is difficult to attach additional components to parallel surfaces, Some dental abutments have grooves 148 in which the length $L_3$ is more or less than 0.125 inches (3.2 mm) (e.g., between 0.1 (2.5 mm) and 0.3 inches (7.6 mm)), the width W is more or less than 0.055 inches (1.4 mm) (e.g., between 0.04 inches (1 mm) and 0.06 inches (1.5 mm)), and/or the depth D is more or less than 0.02 inches (0.51 mm) (e.g., between 0.010 inches (0.254 mm) to 0.030 inches (0.76 mm)). Some dental abutments include other anti-rotation features such as, for example, hexagonal or multi-sided flat surfaces and/or a variety of slots or grooves.

As discussed above, some dental abutments are configured in which the length $L_1$ (between the hemispherical portion of the base 128 and the margin 132) is more or less than 0.16 inches (4 mm) (e.g., between 0.06 inches (1.5 mm) and 0.32 inches (7 mm)).

FIGS. 3A and 3B compare the dental abutment 100 with a dental abutment 200 that has a length $L_1$ that is 0.24 inches (~6 mm). The dental abutment 100 and the abutment 200 have identical configurations except for the differences in the length $L_1$. In particular, the dimensions of the post 120 are the same in both the dental abutment 100 and the abutment 200 such that a single type of dental implant can be used with either abutment. This configuration allows a dentist to set the position of the coronal portion 123 of the dental abutment 100, 200 relative to the gum above an implant regardless of the implant's axial position in the jawbone 112.

Some dental abutments have retention elements 122 that have different perimeters (e.g., diameters for the illustrated dental abutments). FIGS. 4A and 4B compare the dental abutment 100 with a dental abutment 300 in which both length L1 and the diameter of the retention element are smaller than those of the dental abutment 100. It accommodates implant wells that are more parallel for greater retention or wider for greater strength and resistance to metal fatigue and breakage.

Figure 5A:
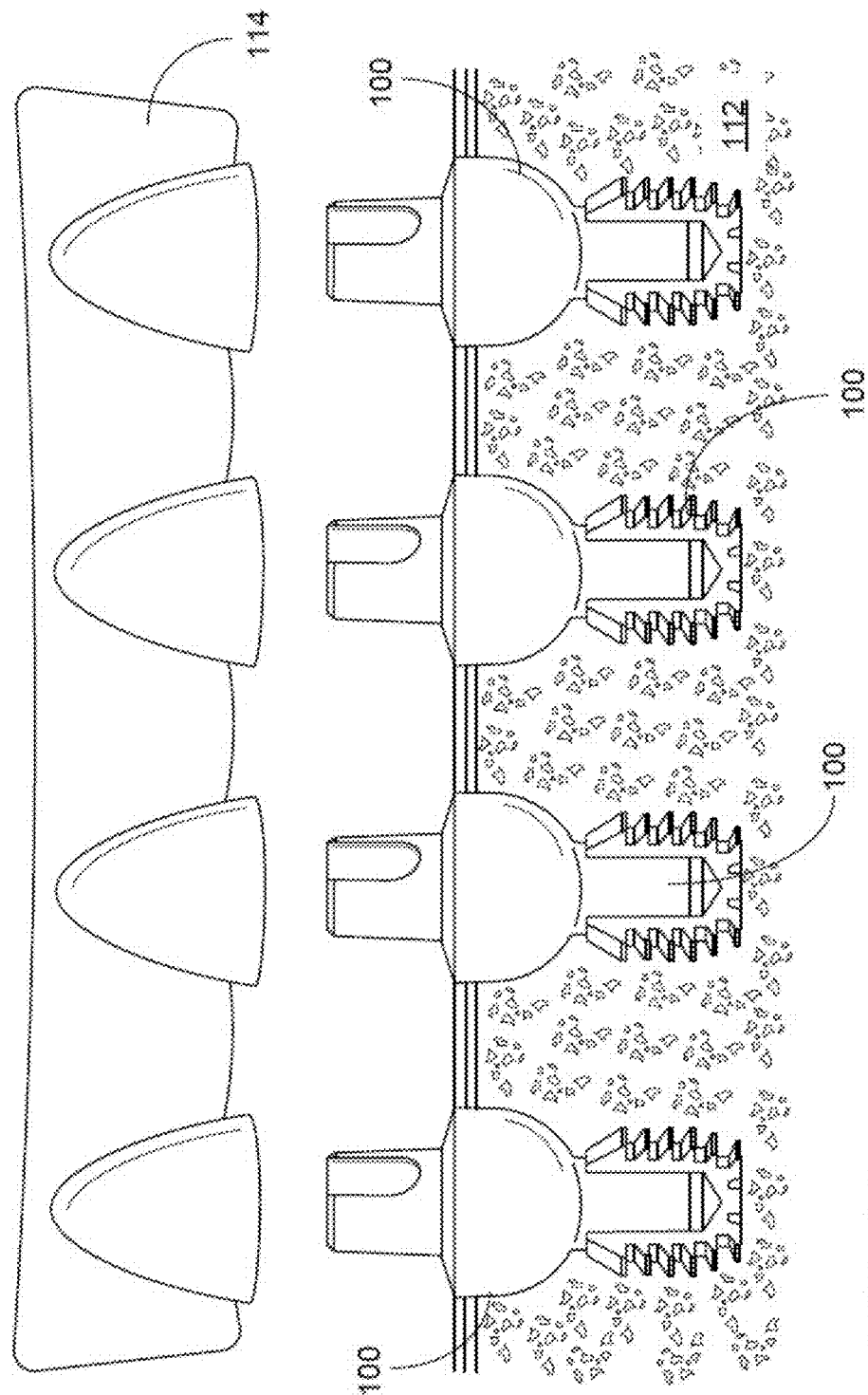
Figure 6B:
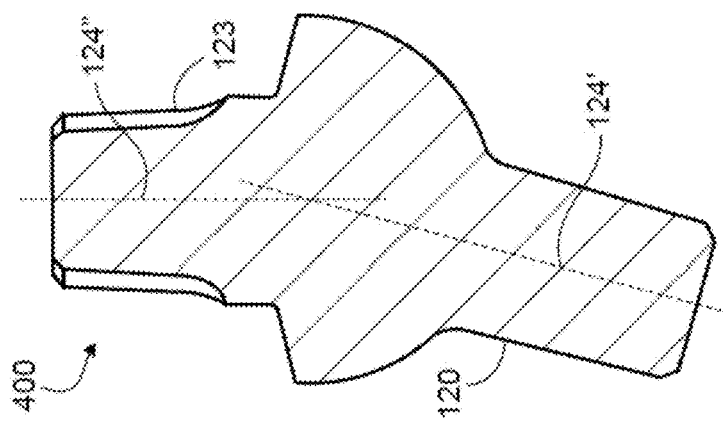
FIGS. 6A and 6B are, respectively, a front view and a side cross-sectional view of an angled dental abutment.
Figure 6A:
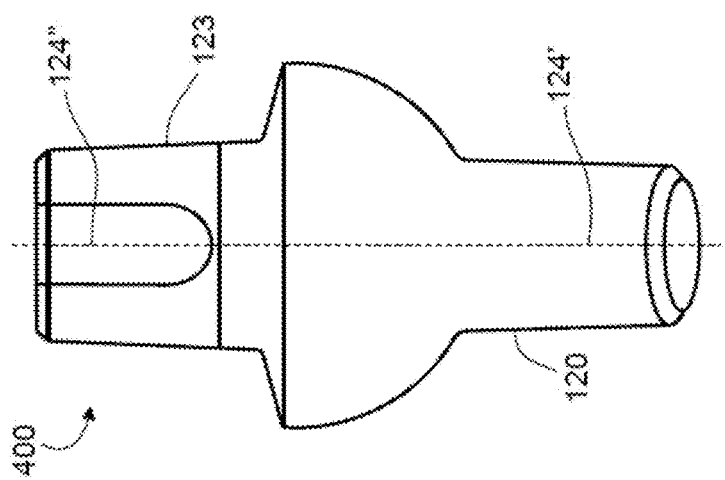
Figure 5C:
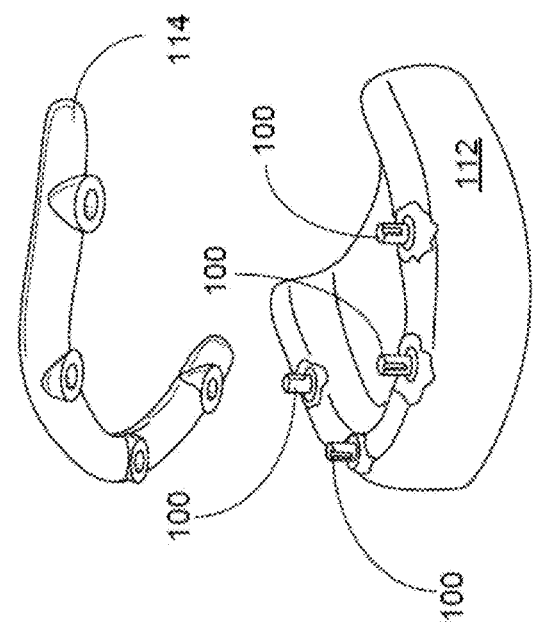

The dental prostheses systems described above include versatile abutments with numerous advantages. Dentists may now make numerous uses and modifications of and departures from the specific embodiments and techniques disclosed herein without departing from the inventive concepts. For example, multiple dental abutments as described above can be used to support a single dental prosthesis. FIGS. 5A-5C show a system in which four dental abutments 100 are used to support a single dental prosthesis 114. In another example, dental abutments can be formed with the features described above but with the post set at angle relative to the coronal portion. FIGS. 6A and 6B show a dental abutment 400 in which an axis 124' of the post 120 set at angle relative to an axis 124" of the coronal portion 123.

FIGS. 7A-13B detail a dental coping designed for use with dental abutments, including, for example, those detailed above and in U.S. application Ser. No. 14/591,654, where is herein incorporated by reference in its entirety. The dental abutment copings described below are designed for cemented fixation to a dental prosthesis. The dental abutment copings include a distal portion defining a cavity sized to accept the head of the dental abutment with a comparable taper and enable the dental prosthesis to be retentively fit onto plurality of dental abutments.

The dental abutment coping is designed to be used in sets of two or more units to provide an retentive frictional interference fit with a corresponding dental abutment, even where the abutments are not parallel. To do so, multiple dental abutment copings secure a dental prosthesis to multiple dental abutments, whereby at least one of copings includes a cavity sized to mate with a dental abutment in a retentive interference fit and the remaining copings mate with the remaining dental abutments in a passive fit. The retentive interference fitment may be, for example, a cylindrical section of the dental coping's cavity concentrically engaging a similarly sized cylindrical portion (e.g., the cylindrical neck 142 described above) of a dental abutment. The passive fit may be, for example, a dental coping's cavity shaped to accept the tapered head of the dental abutment with a comparable taper with reduced (relative to the retentive engagement) or no interfacing with the cylindrical portion of the dental abutment.

Passive and retentive copings can be readily interchanged to provide difference degrees of retention between the dental abutments and a dental prosthesis. Generally, it is noted that a retentive fit coping does not necessarily create a retentive fit with a single dental abutment inserted into it. Instead, in some instances, the use of a plurality of copings including one or more retentive fit copings enables a retentive fit between a dental prosthesis and the corresponding dental abutments, without any single coping/abutment pair of creating a retentive fit. Throughout the application "retentive fit" can refer to both the type of coping (e.g., a retentive fit coping designed to have a higher degree of interference fit between the coping and an abutment) and an overall fitment between a dental prosthesis having the copings and a plurality of corresponding dental abutments where, in some instances, at least one of the copings is a retentive coping.

In a retentive fit coping, the angle and diameter of an internal interface surface determines the 'degree' of interference fit when the coping is placed around the head of a dental abutment. In a retentive fit, more of the interface region is in contact with the cylindrical neck of the abutment. In a passive fit, less of the interface region is in contact with the cylindrical neck of the abutment. In some instances, a plurality of copings are to create a retentive fit between a plurality of dental abutments and a dental prosthesis secured to the copings. In some instances, varying the degree of interference fit between each coping and associated dental abutment varying the overall retentive fit between the dental prosthesis and dental abutments, without any one pair of copings and abutments being in a retentive fit with each other.

The dental abutment copings replace custom-made copings that are typically fabricated in a dental laboratory. The dental abutment coping can be fabricated to achieve a greater accuracy than the custom-made copings. For example, the design of a dental abutment coping can be created digitally in CAD/CAM software and delivered digitally to a milling or printing machine. Additionally, the copings can be digitally scanned and are compatible with CAD/CAM produced component parts. Also, because the copings are digitally fabricated, CAD/CAM produced restorations can consistently fit compatible components.

Figure 7B:
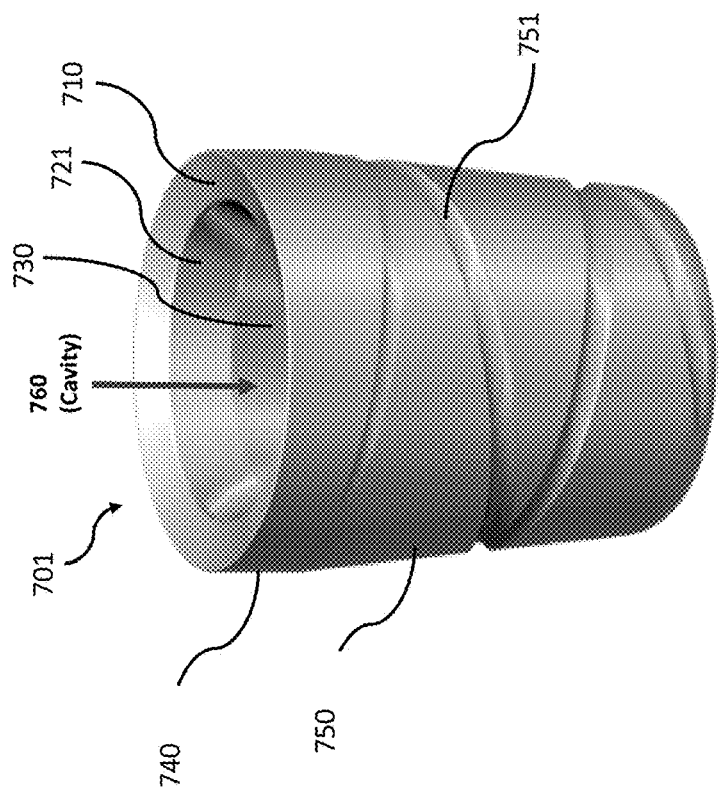
FIGS. 7A and 7B are, respectively, illustrations of retentive and passive fit dental abutment copings.
Figure 7A:
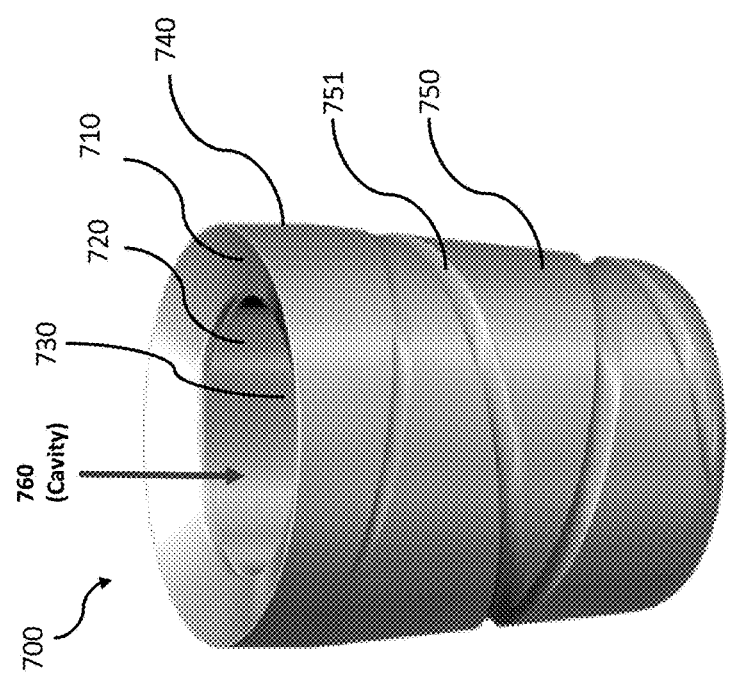

FIGS. 7A and 7B are, respectively, illustrations of retentive and passive fit dental abutment copings. FIG. 7A shows a retentive coping 700 having an inner cavity 760 with a tapered surface 730 and a flat interface surface 720. The flat interface surface is substantially parallel (e.g., aligned within 0.5 degrees) to the axis of the coping. The exterior of the retentive coping 700 includes a tapered exterior surface 750 and a flat exterior surface 740. Two retentive channels 751 are cut into the tapered exterior surface 750. In retentive coping 700, the retentive channels 751 form two counter-rotating spirals around the tapered exterior surface 750. Some copings include more or fewer retentive channels 751 and/or retentive channels in other orientations (e.g., circular rather than spiral retentive channels). The open end of the retentive coping 700 also includes a peripheral surface 710 with an inwardly-facing bevel to accept the shoulder 130 of a dental abutment 100.

Figure 9:
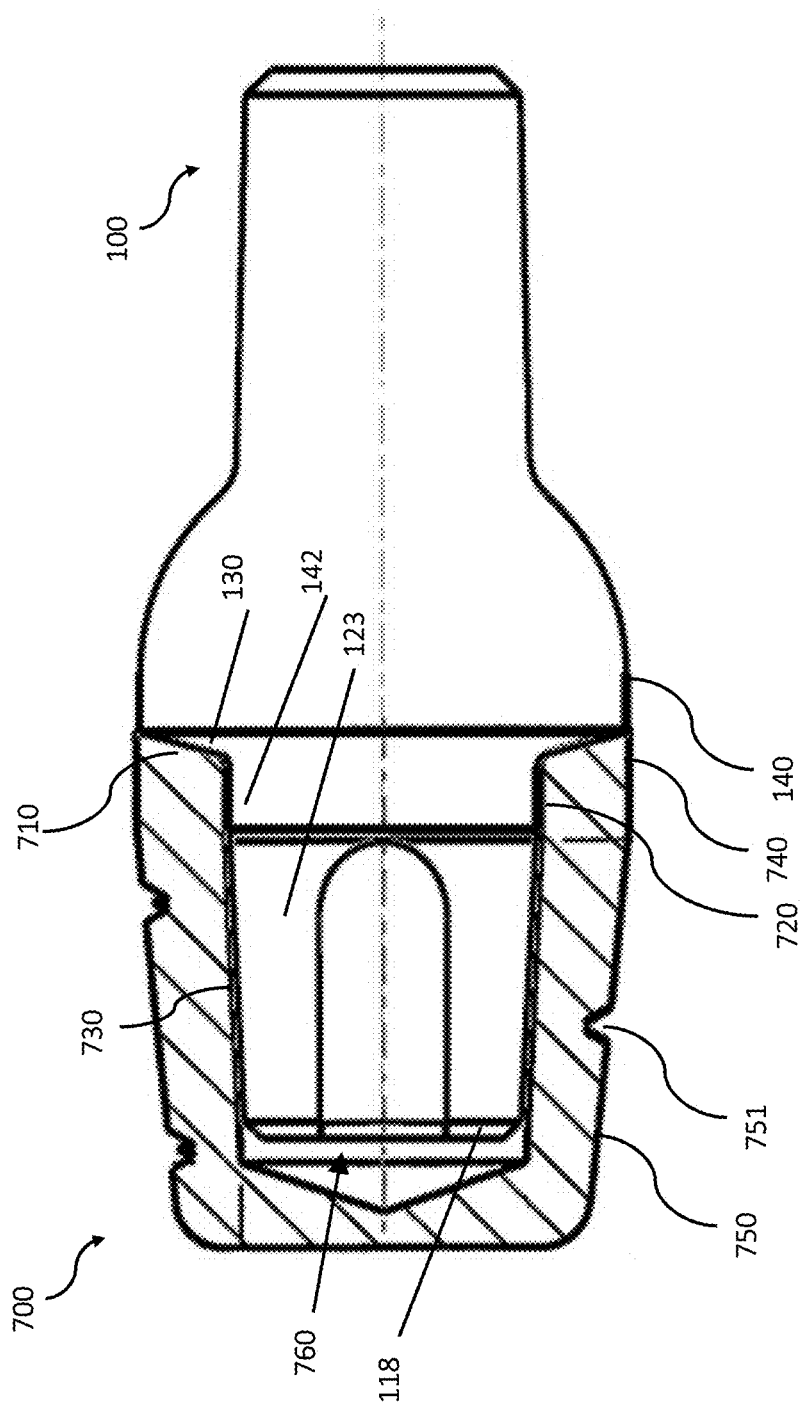
FIG. 9 is an illustration of the retentive fit dental abutment coping of FIG. 8A fitted to the head of a dental abutment.

In operation, and as shown in FIG. 9, the cavity 760 of the retentive coping 700 is sized to accept the coronal end 118 of a dental abutment 100, and the exterior surfaces 740, 750 are sized to be inserted into a dental prosthesis 114. The flat interface surface 720 is sized to accept the cylindrical neck 142 of the dental abutment 100 in a retentive interference fit, also shown in more detail in FIG. 9. The retentive channels 751 provide a location for an adhesive material to be present between the tapered exterior surface 750 and an interface cavity of the dental prosthesis 114, as shown in more detail in FIG. 12.

Figure 11:
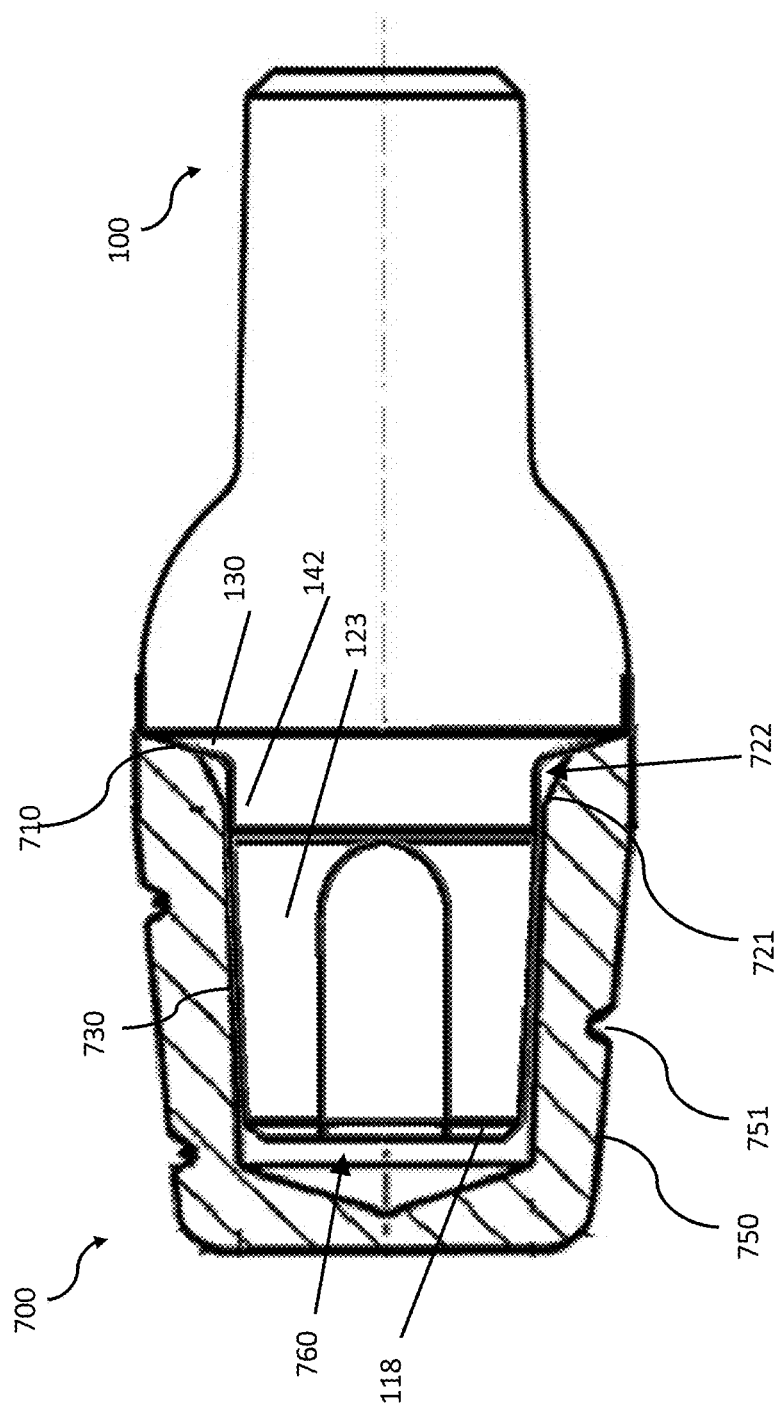
FIG. 11 is an illustration of the retentive-fit dental abutment coping of FIG. 10A fitted on the head of a dental abutment.

FIG. 7B is an illustration of a passive fit coping 701 having an inner cavity 760 with a tapered surface 730 and a beveled interface surface 720. The exterior of the passive coping 701 includes a tapered exterior surface 750 and a flat exterior surface 740. Two retentive channels 751 are cut into the tapered exterior surface 750. The open end of the passive fit coping 701 also includes a peripheral surface 710 with an inwardly-facing bevel. In operation, and as shown in FIG. 11, the cavity 760 of the passive fit coping 701 is sized to accept the coronal end 118 of a dental abutment 100, and the exterior surfaces 740, 750 are sized to be inserted into a dental prosthesis 114. The beveled interface surface 720 is sized to accept the cylindrical neck 142 of the dental abutment 100 without creating a retentive fit, as shown in more detail in FIG. 9. The copings 700, 701 may be manufactured from any material able to be milled or printed, for example a metal such as titanium alloy or stainless steel or composite resins.

Figure 8B:
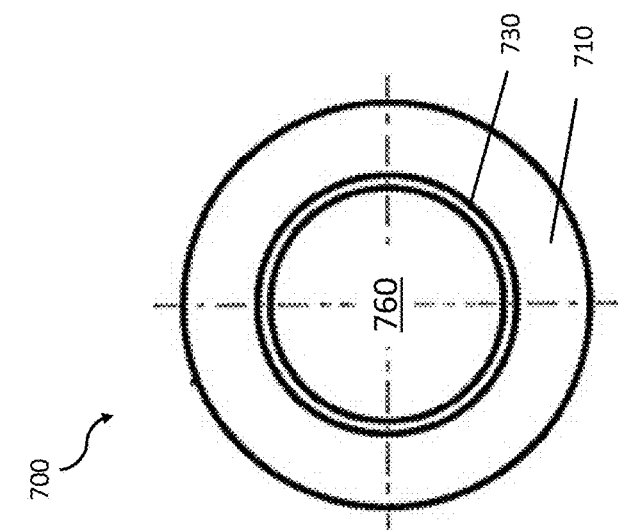
FIGS. 8A and 8B are, respectively, a side cross-section view and a front view of a retentive-fit dental abutment coping.
Figure 8A:
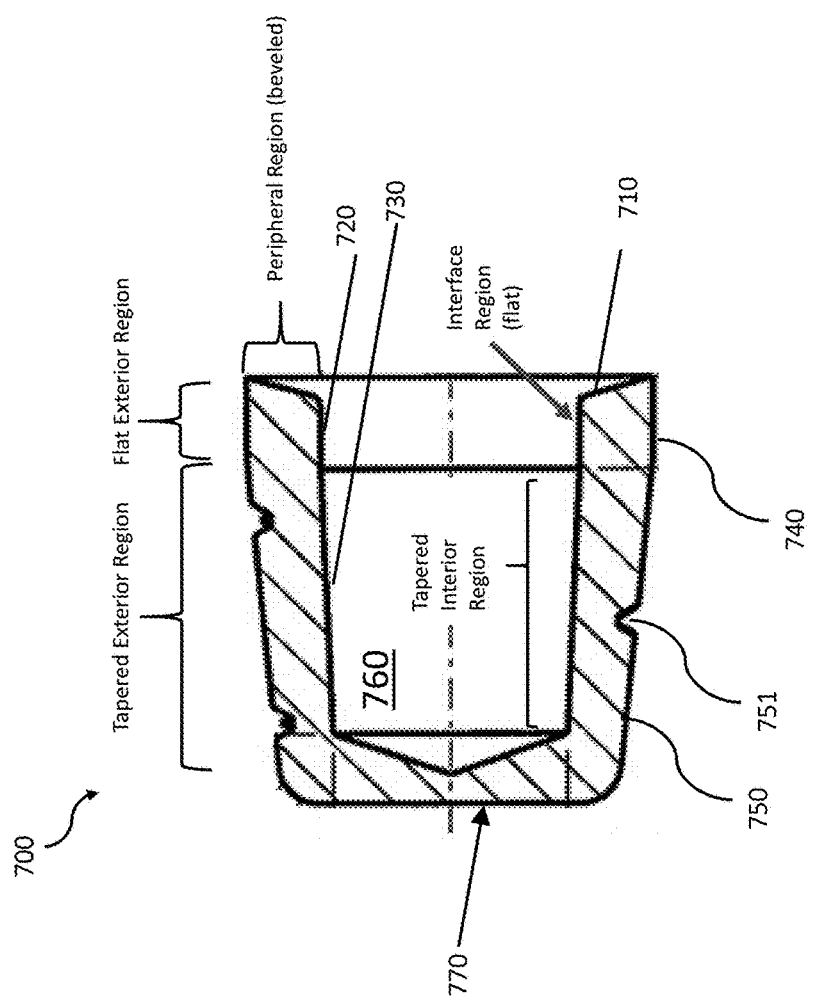

FIGS. 8A and 8B are, respectively, a side cross-section view and a front view of the retentive dental abutment coping 700. The exterior of the retentive coping 700 includes a tapered exterior region extending from a first end 770 to the flat exterior region, which is adjacent to the opposite end, which is open to receive a dental abutment. Although the first end 770 of the retentive dental abutment coping 700 is closed, the first ends of some dental abutment copings are open (e.g., see the dental abutment coping shown in FIGS. 14A-14C).

Other embodiments may include a tapered exterior region extending from the first end 770 to the opposite open end. An interior of the retentive coping 700 includes a tapered interior region and interface region, together defining the cavity 760. In the retentive coping 700, the interface region includes the flat interface surface 720 configured to accept a cylindrical neck of the dental abutment 100 in a retentive interference fit. As shown, the interface surface 720 is parallel or substantially parallel within 0.5° with the longitudinal axis of the retentive coping 700. The tapered interior surface 730 increases the internal diameter of the cavity 760 from the closed or open end 760 to the opposite (open) end of the retentive coping 700.

FIG. 8B is an illustration of a front-view of the retentive coping 700, with the cavity 760 shown as surrounded by the tapered interior surface 730 and the beveled peripheral surface 710. The body of the retentive coping 700 is symmetric about the central axis. In other embodiments, the cavity 760 may be orientated at an angle to the longitudinal axis of the exterior surfaces 740, 750 of the retentive coping 700.

FIG. 9 is an illustration of the retentive dental abutment coping 700 of FIG. 8A fitted to the head of a dental abutment 100. The interior tapered surface 710 of the retentive coping 700 has a taper angle (detailed in FIG. 13B) sized to accept the tapered head 123 of the dental abutment 100. The flat interface surface 720 of the retentive coping 700 is positioned concentrically around the neck 142 of the dental abutment 100. The flat interface surface 720 may have a surface parallel to the longitudinal surface of the retentive coping 700, or may have a small angle to engage the retentive fit as the interface surface is slid onto the neck 142 of the dental abutment 100. The beveled peripheral surface 710 of the retentive coping 700 is against the shoulder 130 of the dental abutment 100.

In operation, the retentive coping 700 is placed onto the dental abutment 100 and the flat interface surface 720 of the retentive coping 700 slides around the neck 142 of the dental abutment 100 until the beveled peripheral surface 710 of the retentive coping 700 is against the shoulder 130 of the dental abutment 100. In this installed configuration, the tolerance (i.e., difference in diameters) between the flat interface surface 720 and the neck 142 of the dental abutment 100 determines the degree of retentive interface fit between the retentive coping 700 and the dental abutment. This tolerance can range from 0 mm to 0.1 mm. In some instances, the flat exterior surface 740 of the coping 700 is not quite the diameter of the outer surface 140 of the universal abutment 100; while the coping 700 still mates with the shoulder 130 of the universal abutment 100, it does not extend all the way to the outer edge 140. This configuration allows a greater volume of material to be milled around the coping 700 while maintaining a more narrow profile.

Figure 10B:
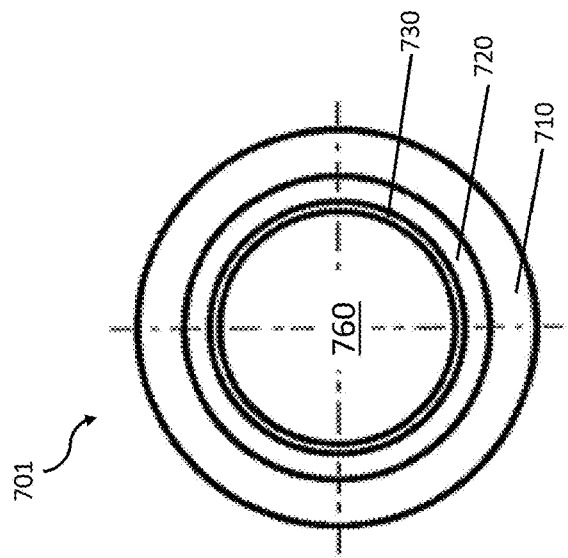
FIGS. 10A and 10B are, respectively, a side cross-section view and a front view of a passive-fit dental abutment coping.
Figure 10A:
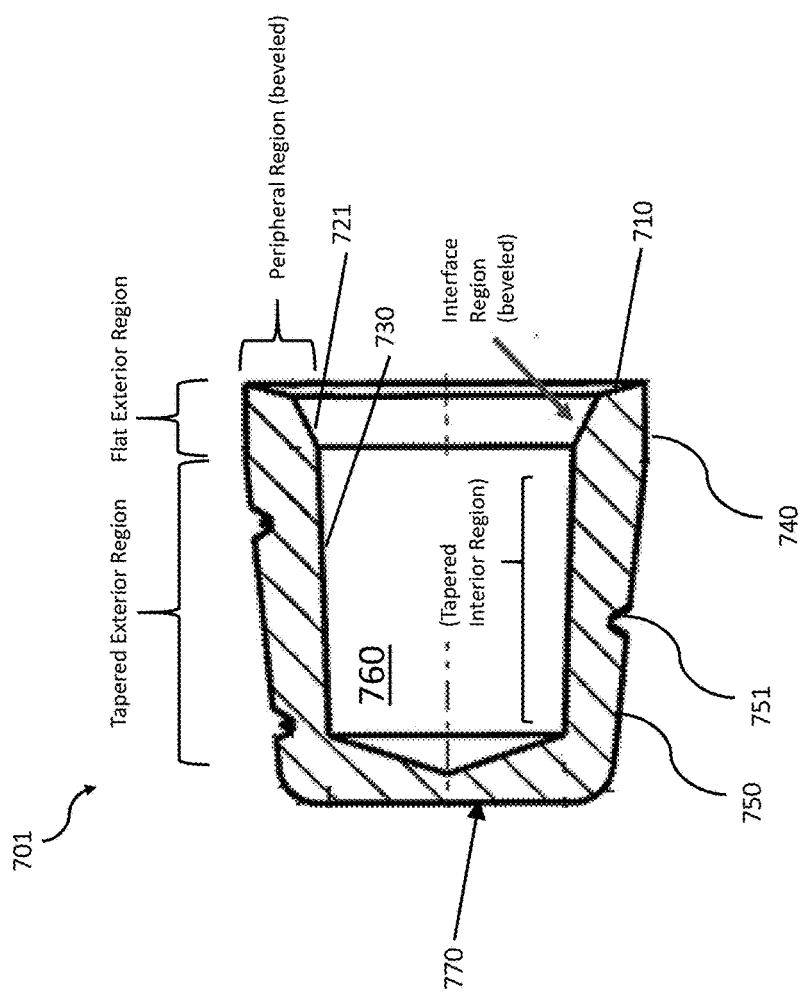

FIGS. 10A and 10B are, respectively, a side cross-section view and a front view of a passive dental abutment coping. FIG. 10A shows the cross-sectional details of the passive coping 701. The exterior of the passive coping 701 includes a tapered exterior region extending from the first end 770 to the flat exterior region, which is adjacent to the opposite open end. Other embodiments may include a tapered exterior region extending from the first end 770 to the opposite open end. An interior of the passive coping 701 includes a tapered interior region and interface region, together forming the cavity 760. In the passive coping 701, the interface region includes the beveled interface surface 721 configured to accept a cylindrical neck of the dental abutment 100 without forming a retentive fit. The beveled interface surface 721 is sized and angled to adjust the degree of the passive vs. retentive fit. This beveled interface surface allows for more insertion angle possibilities for the abutment. A more angled abutment will engage the interface region more. The tapered interior surface 730 increases the internal diameter of the cavity 760 from the closed or open end 760 to the opposite (open) end of the retentive coping 700.

FIG. 10B is an illustration of a front-view of the passive coping 701, with the cavity 760 shown as surrounded by the tapered interior surface 730, the beveled interface surface 721, and the beveled peripheral surface 710. The body of the passive coping 701 is symmetric about the central axis. In other embodiments, the cavity 760 may be orientated at an angle to the longitudinal axis of the exterior surfaces 740, 750 of the passive coping 701.

FIG. 11 is an illustration of the retentive fit dental abutment coping of FIG. 10A fitted on the head of a dental abutment. FIG. 11 shows a passive coping 700 coupled to the head 123 of a dental abutment 100. The interior tapered surface 710 of the passive coping 701 has a taper angle (detailed in FIG. 13B) sized to accept the tapered head 123 of the dental abutment 100. The beveled interface surface 721 of the passive coping 701 is positioned concentrically around the neck 142 of the dental abutment 100. The beveled peripheral surface 710 of the passive coping 701 is against the shoulder 130 of the dental abutment 100.

In operation, the passive coping 701 is placed onto the dental abutment 100 and the beveled interface surface 721 of the passive coping 701 slides around the neck 142 of the dental abutment 100 until the beveled peripheral surface 710 of the passive coping 701 is against the shoulder 130 of the dental abutment 100. In this installed configuration, the beveled interface surface 720 and the neck 142 of the dental abutment 100 form a slight friction fit, and the alignment of passive coping 701 on the dental abutment 100 is determined by the tapered interior surface 730 of the passive coping 701 resting against the tapered head 123 of the dental abutment.

Figure 12:
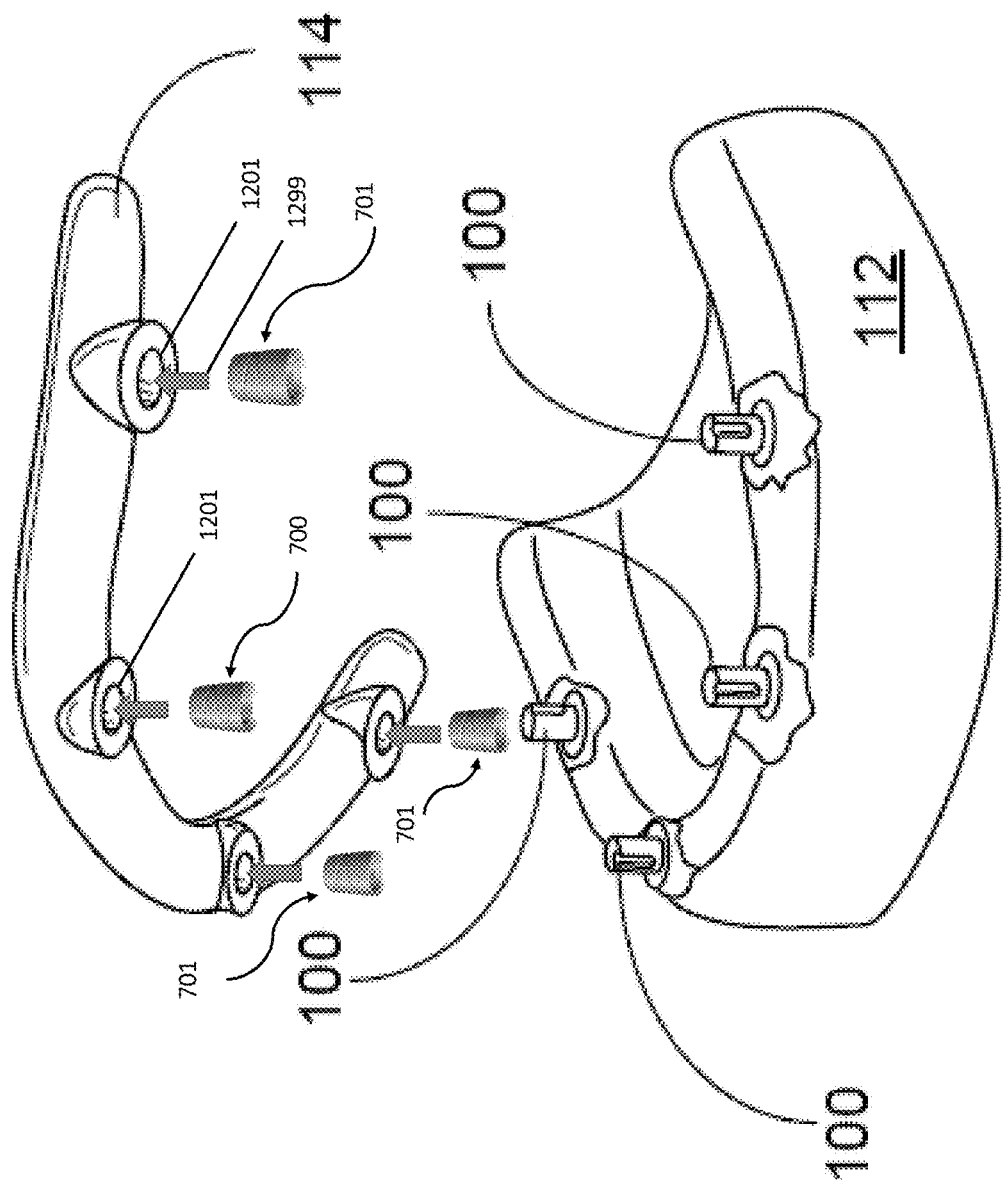
FIG. 12 is an illustration of a plurality of dental abutment copings being inserted into a dental prosthesis to fit the dental prosthesis to multiple dental abutments.

FIG. 12 is an illustration of a plurality of dental abutment copings being inserted into a dental prosthesis to fit the dental prosthesis to multiple dental abutments. FIG. 12 shows a retentive coping 700 and three passive copings 701 positioned between corresponding dental abutments 100 in a patient's jawbone 112 and corresponding interface cavities 1201 in a dental prosthesis 114. In operation, a combination of retentive copings 700 and passive copings 701 are inserted 1299 into the interface cavities 1201 of a dental prosthesis 114 using, for example, a cement placed on the exterior tapered surface 750 of the copings 700, 701 to secure the copings into the dental prosthesis 114. One or more retentive channels 751 may be present on exterior tapered surface 750 to allow more of the cement to be present between the exterior tapered surface 750 of the copings 700, 701 and the interface cavities 1201 of a dental prosthesis 114.

Once secured to the dental prosthesis 114, the copings 700, 701 enable the dental prosthesis 114 to be placed on dental abutments 100 and coupled to the dental abutments 100 with a retentive fit. The combination of retentive copings 700 and passive copings 701 provide the degree of retentive fit and the alignment and support of the dental prosthesis 114 on the abutments 100. Two or more retentive copings 700 may be used for more secure (e.g., tighter) fit, and, in some configurations, the copings 700, 701 may be used to establish a retentive fit between the dental prosthesis 114 and the abutments 100 of a degree that requires a dentist to remove the dental prosthesis 114. In other configurations, the copings 700, 701 may be used to establish a retentive fit of a degree that allows the patient to remove the dental prosthesis 114.

Figures 13A, 13B:
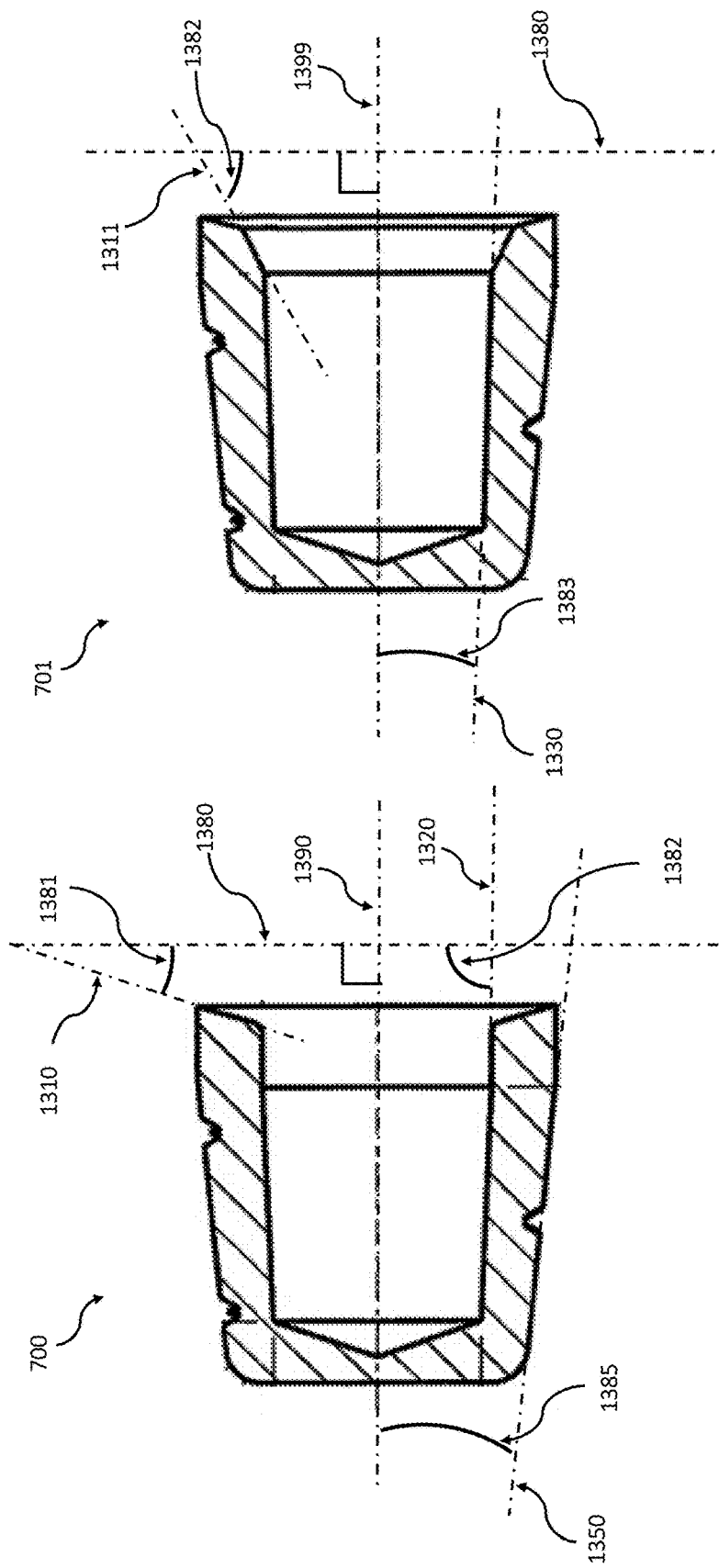
FIGS. 13A and 13B are cross-section views of two dental abutment copings of different configurations showing with the measurement of the surface angles.

FIGS. 13A and 13B are cross-section views of two dental abutment copings of different configurations showing the measurement of the surface angles. In FIG. 13A, the cross-section of the retentive coping 700 of FIG. 8A is shown, and in FIG. 13B, the cross-section of the passive coping 701 of FIG. 10A is shown. In both FIGS. 13A and 13B, the various surfaces (of FIGS. 8A and 10A) are depicted as extended dotted lines (e.g., lines 1310, 1311, 1320, 1330, 1350) for clarify in depicting their relationship to the central longitudinal axis 1390. Additionally, the angle 1381 of the beveled peripheral surface 1310, the angle 1350 of the exterior tapered surface, and the angle 1330 of the interior tapered surface are measured similarly in both the retentive coping 700 of FIG. 13A, and the passive coping 701 of FIG. 13B. The beveled peripheral surface 1310 is orientated inwards (towards the central longitudinal axis 1390) and measured at an angle 1381 to the plane 1380 normal to the central longitudinal axis 1390. The copings 700, 701 are shown symmetric about the central longitudinal axis 1390, but may include in alternate embodiments, for example, anti-rotation features for aligning the copings 700, 701 on a dental abutment 100.

FIG. 13A shows the angle 1382 of the flat interface surface 1320 being perpendicular to the normal plane 1381 of the copings 700, 701 (i.e., parallel to the central longitudinal axis 1390). FIG. 13B shows the beveled interface surface 721 orientated inwards (towards the central longitudinal axis 1390) and measured at an angle 1382 to the normal plane 1380 to the central longitudinal axis 1390.

In an exemplary embodiment, the tapered exterior region 750 defines a taper angle 1385 between 3° and 8°. The angle 1381 of the beveled peripheral surface is at least between 12° and 18° relative to the longitudinal axis 1390. The angle of the beveled interface surface 721 is at least between 20° and 30° relative to the normal plane 1380.

FIGS. 14A and 14B are, respectively, perspective and side cross-section views of a retentive-fit dental abutment coping having a thru opening. FIG. 14A shows a retentive-fit dental abutment coping 1400 with opposing first and second open ends 1470a,b forming a thru opening 1460. The exterior surface 1450 of the coping 1400 includes a retentive channels 1451 to contain a mechanical or adhesive bonding agent. FIG. 14B shows a side cross-section of the retentive-fit dental abutment coping 1400. The thru opening 1460 is visible extending from the first open end 1470a to the second end open 1470b of the retentive-fit dental abutment coping 1400. The peripheral surface 710, interface surface 720 and tapered interior surface 730 of the retentive-fit dental abutment coping 1401 are sized and shaped similarly to the closed-end retentive-fit dental abutment copings 700 (FIGS. 7A, 8A, and 9) and provide similar functions. Some passive-fit retentive-fit dental abutment copings (not shown) also have a thru opening configuration with corresponding interior and peripheral surfaces as the closed-end passive-fit dental abutment coping 701 (FIGS. 7B, 10A, and 11).

Figure 14C:
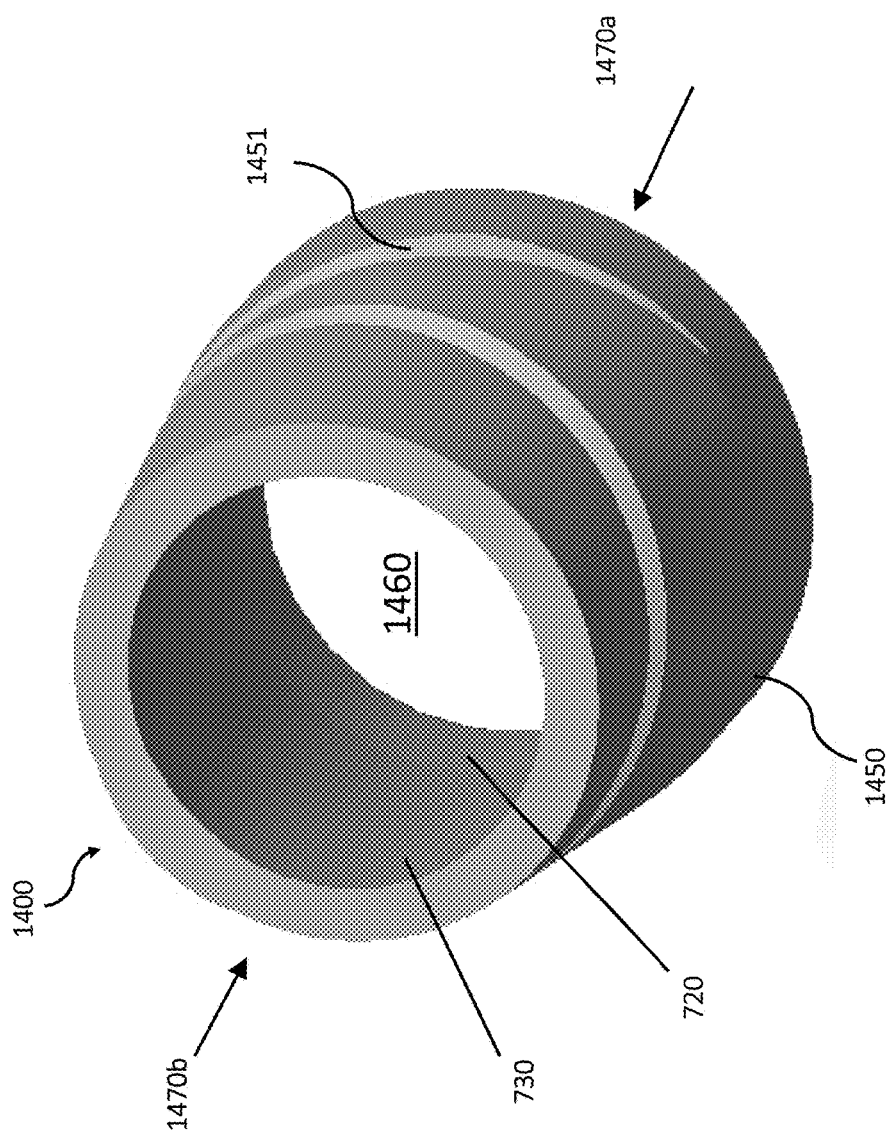
FIG. 14C is a front perspective view of the retentive-fit dental abutment coping having a thru opening of FIGS. 14A and 14B.

FIG. 14C is a front perspective view of the retentive-fit dental abutment coping having a thru opening of FIGS. 14A and 14B.

In either of the closed-end 700, 701 and thru opening copings 1400, a portion of the end of the coping body distal to the peripheral surface 710, for example, closed end 770 and first open end 1470a) may form a hemispherical or domed section, or other rounded shape, to improve insertion of the coping 700, 701, 1400 into a dental prosthesis 114.

Consequently, the claims are to be construed as embracing each and every novel feature and novel combination of features presented in or possessed by the apparatus and techniques herein disclosed.

FIGS. 15A-D are perspective and cross-sections views of a passive and retentive copings having an exterior shoulder. FIGS. 15A and 14B are, respectively, side cross-section and perspective views of a retentive-fit dental abutment coping having a thru opening. FIG. 14A shows a retentive-fit dental abutment coping 1500 with a hemispherical front end 1570 and a protruded flat exterior surface 1540 defining a shoulder 1541 at the open end of the coping 1500. In some instances, the shoulder 1541 enables more restorative material to be built around the coping 1500. In some instances, the height of the shoulder 1541 (e.g., the distance from the protruded flat exterior surface 1540 to the tapered exterior surface 1550) is between 0 mm-2 mm. The exterior surface 1550 of the coping 1500 includes a retentive channels 1551 to contain a mechanical or adhesive bonding agent. FIG. 15A shows a side cross-section of the retentive-fit dental abutment coping 1501. The cavity opening 1560 is visible extending from the hemispherical front end 1570 of the retentive-fit dental abutment coping 1500. The peripheral surface 710, interface surface 720 and tapered interior surface 730 of the retentive-fit dental abutment coping 1500 are sized and shaped similarly to the previously described retentive-fit dental abutment coping 700 (FIGS. 7A, 8A, and 9) and provide similar functions. FIGS. 15C and 15D show a passive-fit retentive-fit dental abutment coping 1501 also having a hemispherical front end 1570 and a protruded flat exterior surface 1540 defining a shoulder 1541 at the open end of the coping 1501, with similar interior and peripheral surfaces as the retentive-fit dental abutment coping 1500.

There has been described novel apparatus and techniques in connection with dental implantation. It is evident that those skilled in the art may make numerous modifications of and departures from the specific apparatus and techniques herein disclosed without departing from the inventive concepts. Consequently, the invention is to be construed as embracing each and every novel concept and combination of concepts disclosed herein and limited only by the spirit and scope of the appended claims.

What is claimed is:

1. A dental abutment coping for securing a dental prosthesis to a dental abutment, the dental abutment coping comprising:
   a body extending from a first end to a second end along a longitudinal axis, the body defining a cavity extending from an opening in the second end of the dental abutment coping, the body comprising:

an exterior surface adapted to be inserted into a corresponding interface cavity of the dental prosthesis;

a peripheral region of the second end, the peripheral region extending around the opening and comprising a beveled surface oriented towards the longitudinal axis at an angle relative to the longitudinal axis; and an interior surface sized to accept a head of the dental abutment, the interior surface having a tapered interior region and an interface interior region, the interface interior region being between the peripheral region and the tapered interior region, and the tapered interior region defining an increasing internal diameter of the cavity between a distal end of the cavity and the interface interior region;

wherein the exterior surface includes a tapered exterior region;

a flat exterior region parallel to the longitudinal axis;

wherein the tapered exterior region extends from the first end of the body to the flat exterior region, the tapered exterior region defining an increasing exterior diameter of the body along the length towards the second end, and wherein the flat exterior region extends from the tapered exterior region to the beveled surface of the peripheral region of the second end.

2. The dental abutment coping of claim 1, wherein the angle of the beveled surface is at least between 12° and 18° relative to the longitudinal axis.

3. The dental abutment coping of claim 1, wherein the exterior surface defines one or more channels configured to contain a cement for attaching the exterior surface to the dental prosthesis.

4. The dental abutment coping of claim 3, wherein the one or more channels comprise a counter-rotating spiral channel.

5. The dental abutment coping of claim 1, wherein the tapered exterior region defines a taper angle between 3° and 8°.

6. The dental abutment coping of claim 1, wherein the dental abutment coping is symmetric about the longitudinal axis with respect to the longitudinal axis.

7. The dental abutment coping of claim 1, wherein the interface interior region is positioned adjacent to both the peripheral region and the tapered interior region.

8. The dental abutment coping of claim 1, wherein the interface interior region comprises an interface surface substantially parallel to the longitudinal axis.

9. The dental abutment coping of claim 1, wherein the beveled surface of the peripheral region is a first beveled surface, and wherein the interface interior region comprises a second beveled surface oriented towards the longitudinal axis at an angle relative to a plane that is normal to the longitudinal axis, the angle of the second beveled surface being greater than the angle of the first beveled surface.

10. The dental abutment coping of claim 1, wherein the first end is a closed end and the second end is an open end.

11. The dental abutment coping of claim 1, wherein the cavity of the body extends from the opening in the second end to a corresponding opening in the first end.

12. The dental abutment coping of claim 1, wherein the body is a milled body, a machined body, or a printed body.

13. The dental abutment coping of claim 1, wherein the body is constructed by an additive manufacturing process.

14. A dental prosthesis system comprising:

a plurality of dental abutments;

a dental prosthesis including a plurality of interface cavities; and a first dental abutment coping, comprising:

a body extending from a first end to a second end along a first longitudinal axis, the body defining a cavity extending from an opening in an open end of the first dental abutment coping, the body comprising:

an exterior surface adapted to be inserted into one of the interface cavities of the dental prosthesis, a peripheral region of the second end, the peripheral region extending around the opening and comprising a first beveled surface oriented towards the first longitudinal axis, and an interior surface sized to accept a head of each of the plurality of dental abutments, the interior surface having a tapered interior region and an interface interior region, the interface interior region being between the peripheral region and the tapered interior region, and the tapered interior region defining an increasing internal diameter of the cavity between a distal end of the cavity and the interface interior region, the interface interior region of the first coping comprising an interface surface substantially parallel to the first longitudinal axis;

a second dental abutment coping, comprising:

a body extending from a first end to a second end along a second longitudinal axis, the body defining a cavity extending from an opening in the second end of the second dental abutment coping, the body comprising:

an exterior surface adapted to be inserted into one of the interface cavities of the dental prosthesis, a peripheral region of the second end, the peripheral region extending around the opening and comprising a first beveled surface oriented towards the second longitudinal axis, and an interior surface sized to accept a head of each of the plurality of dental abutments, the interior surface having a tapered interior region and an interface interior region, the interface interior region being between the peripheral region and the tapered interior region, and the tapered interior region defining an increasing internal diameter of the cavity between a distal end of the cavity and the interface interior region, and the interface region of the second coping comprising a second beveled surface oriented towards the second longitudinal axis at an angle relative to the second longitudinal axis;

wherein the plurality of dental abutments each comprises:

a retention element with a base oriented towards an apical end of the dental implant and a shoulder oriented towards a coronal end of the dental abutment at an angle relative to a third longitudinal axis such that the perimeter of the retention element increases with increasing distance from the coronal end of the dental abutment through the region of the shoulder, a post extending from the apical end of the dental abutment to the base of the retention element, and the head extending from the coronal end of the dental abutment to the shoulder of the retention element.

15. The system of claim 14, wherein the exterior surface of the first and second dental abutment copings defines one or more channels containing mechanical bonding to the exterior surface to the dental prosthesis.

16. The system of claim 14, wherein the exterior surface of the first and second dental abutment copings includes a tapered exterior region extending from the first end a length of the longitudinal axis, the tapered exterior region defining an increasing exterior diameter of the body along the length.

17. The system of claim 16, wherein the exterior surface further includes a flat exterior region along the first longitudinal axis, the tapered exterior region extending from the first end to the flat exterior region, the tapered exterior region defining an increasing exterior diameter of the body from the first end to the flat exterior region.

18. The system of claim 14, wherein the head of each of the plurality of dental abutments has a cone angle between 3° and 8°, and wherein the tapered exterior region of the first and second copings defines a taper angle between 2° and 4.

19. The system of claim 14, wherein the shoulder of each of the plurality of dental abutments being oriented at an angle of at least 12.5° relative to a second longitudinal axis between the coronal end and the apical end, and wherein the angle of the first beveled surface of the first and second copings is at least 12.5° relative to the longitudinal axis.

20. The system of claim 14, wherein each dental abutment further comprises a cylindrical neck element positioned between the head and the retention element, the interface surface of the first coping accepting the neck element of a first one of the plurality of dental abutments in a retentive friction fit, and the second beveled surface of the second coping accepting the neck element of a second one of the plurality of dental abutments.

21. The system of claim 14, wherein the first dental abutment coping is symmetric about the first longitudinal axis and the second dental abutment coping is symmetric about the second longitudinal axis.

22. The system of claim 14, wherein the first end of the first and second dental abutment copings is a closed end and the second end of the first and second dental abutment copings is an open end.

23. The system of claim 14, wherein the cavity of the first and second dental abutment copings is a thru opening extending from the opening in the second end to a corresponding opening in the first end.

24. The system of claim 14, wherein the body of the first and second dental abutment copings is one of a milled body, a machined body, and a printed body.

25. The system of claim 14, wherein the body of the first and second dental abutment copings is constructed from an additive manufacturing process.

* * * * *

UNITED STATES PATENT AND TRADEMARK OFFICE
CERTIFICATE OF CORRECTION

PATENT NO. : 10,136,967 B2
APPLICATION NO. : 15/065460
DATED : November 27, 2018
INVENTOR(S) : Vincent J. Morgan and Robert E. Vasile Page 1 of 1

It is certified that error appears in the above-identified patent and that said Letters Patent is hereby corrected as shown below:

In the Claims

Column 15 Line 13 Claim 18, delete "4." and insert -- 4°. --

Signed and Sealed this
Fifth Day of February, 2019

Andrei Iancu
*Director of the United States Patent and Trademark Office*